United States Patent
Izumi et al.

(10) Patent No.: US 11,566,273 B2
(45) Date of Patent: Jan. 31, 2023

(54) METHOD FOR PRODUCING CELL CONTAINED BASE AND METHOD FOR EVALUATING EQUIPMENT

(71) Applicant: RICOH COMPANY, LTD., Tokyo (JP)

(72) Inventors: Satoshi Izumi, Tokyo (JP); Manabu Seo, Kanagawa (JP); Takahiko Matsumoto, Kanagawa (JP); Hiroki Somada, Shizuoka (JP); Ryuya Mashiko, Tokyo (JP); Takeshi Orito, Kanagawa (JP); Hiroki Nakae, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 60 days.

(21) Appl. No.: 16/007,274

(22) Filed: Jun. 13, 2018

(65) Prior Publication Data
US 2018/0363028 A1 Dec. 20, 2018

(30) Foreign Application Priority Data

Jun. 14, 2017 (JP) .............................. JP2017-117091
May 18, 2018 (JP) .............................. JP2018-096636

(51) Int. Cl.
*G01N 15/14* (2006.01)
*C12M 1/42* (2006.01)
(Continued)

(52) U.S. Cl.
CPC ............ *C12Q 1/6806* (2013.01); *C12M 35/02* (2013.01); *C12M 47/04* (2013.01); *C12Q 1/686* (2013.01);
(Continued)

(58) Field of Classification Search
CPC ............ C12Q 1/6806; C12Q 2565/626; C12Q 2545/113; C12M 35/02; C12M 47/04;
(Continued)

(56) References Cited

U.S. PATENT DOCUMENTS

| | | | |
|---|---|---|---|
| 5,641,457 A * | 6/1997 | Vardanega | B01L 1/04 250/461.2 |
| 2007/0059763 A1 * | 3/2007 | Okano | G01N 33/566 435/7.1 |

(Continued)

FOREIGN PATENT DOCUMENTS

| | | |
|---|---|---|
| JP | 2008-000693 | 1/2008 |
| JP | 2012-505406 | 3/2012 |

(Continued)

OTHER PUBLICATIONS

Marinov et al "From single-cell to cell-pool transcriptomes: Stochasticity in gene expression and RNA splicing" GEnome Research, 2014, 24: 496-510. (Year: 2014).*

(Continued)

*Primary Examiner* — Robert T. Crow
(74) *Attorney, Agent, or Firm* — Grüneberg and Myers PLLC

(57) ABSTRACT

Provided is a method for producing a cell contained base, the method being capable of providing a cell contained base highly accurately controlled in number of nucleic acid molecules contained in a low-concentration nucleic acid standard sample, the method including a liquid droplet discharging step of discharging a cell suspension in the form of a liquid droplet with a liquid droplet discharging unit onto a base including at least one cell contained region; a cell number counting step of counting a number of cells contained in the liquid droplet with a plurality of sensors from two or more directions while the liquid droplet is flying into the cell contained region; and a liquid droplet landing step of landing the liquid droplet in the at least one cell contained region in a manner that a predetermined number of cells are located in the at least one cell contained region.

11 Claims, 16 Drawing Sheets

Specification includes a Sequence Listing.

(51) Int. Cl.
*C12Q 1/6806* (2018.01)
*C12M 1/00* (2006.01)
*G01N 35/10* (2006.01)
*C12Q 1/686* (2018.01)

(52) U.S. Cl.
CPC ........... *G01N 15/14* (2013.01); *G01N 15/147* (2013.01); *G01N 35/10* (2013.01); *G01N 35/1016* (2013.01); *C12Q 2545/10* (2013.01); *G01N 2015/1445* (2013.01); *G01N 2015/1461* (2013.01); *G01N 2015/1481* (2013.01); *G01N 2015/1486* (2013.01); *G01N 2035/1041* (2013.01)

(58) Field of Classification Search
CPC ....... C12M 23/12; G01N 15/14; G01N 15/06; G01N 2015/0693; G01N 2015/1481; G01N 2015/1486; G01N 35/10; G01N 15/1459; G01N 15/1463; G01N 2015/1445; G01N 2015/149; G01N 2035/1034; G01N 15/1404; G01N 2035/1039; G01N 2015/1402; G01N 2015/1406; G01N 2015/1006; B01L 3/0268; B01L 3/502761; B01L 2200/0647; B01L 2200/148; B41J 2202/15; B41J 2/16579
See application file for complete search history.

(56) References Cited

U.S. PATENT DOCUMENTS

| | | |
|---|---|---|
| 2010/0090677 A1 | 4/2010 | Britton et al. |
| 2014/0306122 A1 | 10/2014 | Norton et al. |
| 2014/0307940 A1 | 10/2014 | Norton et al. |
| 2014/0309795 A1 | 10/2014 | Norton et al. |
| 2016/0244828 A1* | 8/2016 | Mason ................. C12Q 1/6874 |
| 2016/0258796 A1 | 9/2016 | Norton et al. |
| 2018/0051330 A1 | 2/2018 | Amiss et al. |
| 2018/0202846 A1 | 7/2018 | Norton et al. |

FOREIGN PATENT DOCUMENTS

| | | |
|---|---|---|
| JP | 2014-033658 A | 2/2014 |
| JP | 2015-195735 A | 11/2015 |
| JP | 2015-198652 | 11/2015 |
| JP | 2016-521362 | 7/2016 |
| JP | 2018-000112 | 1/2018 |
| JP | 2018-001098 | 1/2018 |
| JP | 2018-009956 | 1/2018 |
| JP | 2018-017700 | 2/2018 |
| JP | 2018-087770 A | 6/2018 |
| WO | WO 2016/160823 A1 | 10/2016 |
| WO | 2017/130707 A1 | 8/2017 |

OTHER PUBLICATIONS

U.S. Appl. No. 15/846,393, filed Dec. 19, 2017.
Extended European Search Report dated Feb. 18, 2019 in Patent Application No. 18177340.9, 12 pages.
Moon, S. et al., "Drop-on-Demand Single Cell Isolation and Total RNA Analysis", Plos One, XP055518360, vol. 6, No. 3, Mar. 11, 2011, pp. 1-10.
Zhang, Q. et al., "Development of a facile droplet-based single-cell isolation platform for cultivation and genomic analysis in microorganisms", Scientific Reports, XP055518191, vol. 7, No. 1, Jan. 23, 2017, pp. 1-11.
Japanese Office Action dated Feb. 1, 2022 in Japanese Application No. 2018-096636, with English translation, 12 pages.

* cited by examiner $350_1$  $350_2$ $350_1$  $350_2$

SEQUENCE LISTING

<160> NUMBER OF SEQ ID NOS: 1

<210> SEQ ID NO 1
<211> LENGTH: 500
<212> TYPE: DNA
<213> ORGANISM: Norwalk virus -continued

```
<400> SEQUENCE: 1
tgtcatcaaa ttgccaataa aagttggcat gaacacaata gaagatggcc ccctcatcta      60
tgctgagcat gctaaatata agaatcattt tgatgcagat tatacagcat gggactcaac     120
acaaaataga caaattatga cagaatcctt ctccattatg tcgcgcctta cggcctcacc     180
agaattggcc gaggttgtgg cccaagattt gctagcacca tctgagatgg atgtaggtga     240
ttatgtcatc agggtcaaag aggggctgcc atctggattc ccatgtactt cccaggtgaa     300
cagcataaat cactggataa ttactctctg tgcactgtct gaggccactg gtttatcacc     360
tgatgtggtg caatccatgt catatttctc attttatggt gatgatgaga ttgtgtcaac     420
tgacatagat tttgacccag cccgcctcac tcaaattctc aaggaatatg gcctcaaacc     480
aacaaggcct gacaaaacag                                                 500
```

METHOD FOR PRODUCING CELL CONTAINED BASE AND METHOD FOR EVALUATING EQUIPMENT

CROSS-REFERENCE TO RELATED APPLICATIONS

The present application claims priority under 35 U.S.C. § 119 to Japanese Patent Application No. 2017-117091 filed Jun. 14, 2017 and Japanese Patent Application No. 2018-096636 filed May 18, 2018. The contents of which are incorporated herein by reference in their entirety.

BACKGROUND OF THE INVENTION

Field of the Invention

The present disclosure relates to a method for producing a cell contained base and a method for evaluating equipment.

Description of the Related Art

In recent years, increased sensitivity of analytical techniques has enabled measurement of measurement targets in unit of the number of molecules, and industrial application of gene detection techniques for detecting trace nucleic acids to foods, environmental audits, and medical care has been demanded.

For example, owing to the technological characteristics of polymerase chain reactions (PCR) often used in the field of molecular biology studies, polymerase chain reactions (PCR) are said to be theoretically capable of amplifying a nucleic acid even if the nucleic acid includes only 1 molecule.

In the detection of such trace genes by quantitative analyses, there is a need for using standard samples, and there has been proposed a method for diluting a DNA fragment having a specific base sequence by a limiting dilution method and selecting a diluted solution including the intended number of molecules based on the result of real-time PCR of the obtained diluted solutions (for example, see Japanese Unexamined Patent Application Publication No. 2014-33658).

There has also been proposed a method for introducing a specific copy number of DNA fragments into cells by a gene recombination technique, culturing the cells, and isolating the cultured cells to produce a standard sample containing the intended copy number of DNA fragments (for example, see Japanese Unexamined Patent Application Publication No. 2015-195735).

Moreover, techniques for discharging a solution containing a plurality of cells in the form of liquid droplets by ink jetting are also being developed. What matters when discharging liquid droplets containing particles, which are represented by cells, is to sense how many particles are contained in the liquid droplets to be discharged.

As a method including this function, there has been proposed a discharging method of irradiating a discharged liquid droplet with laser light and capturing the image of or measuring the light volume of the discharged liquid droplet with a CCD camera or a photodiode to measure the number of cells in the discharged liquid droplet (for example, see Japanese Unexamined Patent Application Publication No. 2008-693).

SUMMARY OF THE INVENTION

According to one aspect of the present disclosure, a method for producing a cell contained base includes a liquid droplet discharging step of discharging a cell suspension in the form of a liquid droplet with a liquid droplet discharging unit onto a cell contained base including at least one cell contained region, a cell number counting step of counting a number of cells contained in the liquid droplet with a plurality of sensors from two or more directions while the liquid droplet is flying into the cell contained region, and a liquid droplet landing step of landing the liquid droplet in the at least one cell contained region in a manner that a predetermined number of cells are located in the at least one cell contained region.

DESCRIPTION OF THE EMBODIMENTS

Figure 1:
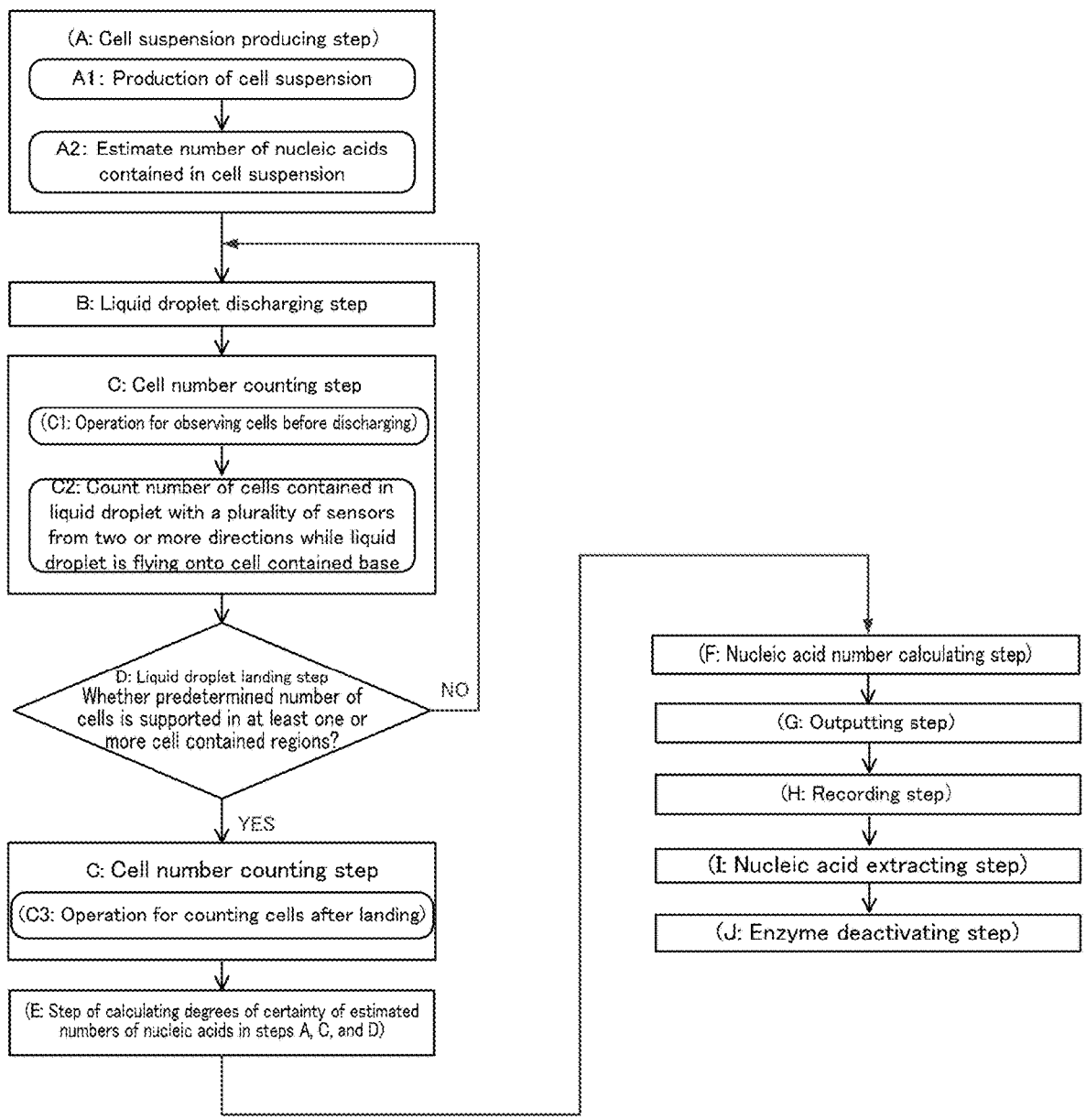
FIG. 1 is a flowchart illustrating an example of each step of the present disclosure.

The present disclosure has an object to provide a method for producing a cell contained base, the method being capable of providing a cell contained base highly accurately controlled in the number of nucleic acid molecules contained in a low-concentration nucleic acid standard sample.

The present disclosure can provide a method for producing a cell contained base, the method being capable of providing a cell contained base highly accurately controlled in the number of nucleic acid molecules contained in a low-concentration nucleic acid standard sample.

(Method for Producing Cell Contained Base)

A method for producing a cell contained base of the present disclosure includes a liquid droplet discharging step of discharging a cell suspension in the form of a liquid droplet with a liquid droplet discharging unit onto a cell contained base including at least one or more cell contained regions, a cell number counting step of counting a number of cells contained in the liquid droplet with a plurality of sensors from two or more directions while the liquid droplet is flying into the cell contained regions, and a liquid droplet landing step of landing the liquid droplet in the at least one or more cell contained regions in a manner that a predetermined number of cells are contained in the at least one or more cell contained regions, preferably includes a cell suspension producing step and a nucleic acid extracting step, more preferably includes a step of calculating degrees of certainty of estimated numbers of nucleic acids in the cell suspension producing step, the liquid droplet landing step, and the cell number counting step, an outputting step, and a recording step, and further includes other steps as needed.

The present inventors have obtained the following finding from the studies on the method for producing a cell contained base, capable of providing a cell contained base highly accurately controlled in the number of nucleic acid molecules contained in a low-concentration nucleic acid standard sample.

For example, in existing methods for producing nucleic acid solution samples, low-concentration nucleic acid standard samples are prepared by a limiting dilution method. Therefore, there may stochastically occur cases where no nucleic acids are contained in the samples, or there is a problem that it is difficult to contain a desired number of nucleic acid molecules in the samples.

Further, for example, in the existing methods for producing standard samples, cells into which a specific copy number of DNA fragments have been introduced are isolated by manual procedures. Therefore, there is a problem that it is difficult to prepare a sample containing a desired number of nucleic acid molecules due to indeterminate factors that may occur during isolation.

Furthermore, for example, in existing discharging methods, the number of cells contained in a liquid droplet discharged is counted with a counting unit. However, there is a problem that it is difficult to count the cells in the liquid droplet accurately, because the cells in the liquid droplet is only counted from 1 direction.

The present inventors have found it possible to obtain a cell contained base highly accurately controlled in the number of nucleic acid molecules contained in a low-concentration nucleic acid standard sample, by discharging a cell suspension in the form a liquid droplet and counting the number of cells contained in the liquid droplet with a plurality of sensors from two or more directions.

A flowchart of an example of the method for producing a cell contained base (a plate with a known cell number or a plate with nucleic acids already extracted) of the present disclosure is illustrated in FIG. 1, and each step will be described below.

As illustrated in FIG. 1, the method for producing a cell contained base of the present disclosure includes B: a liquid droplet discharging step, C: a cell number counting step, and D: a liquid droplet landing step, and as needed, includes A: a cell suspension producing step, E: a step of calculating degrees of certainty of estimated numbers of nucleic acids in the steps A to D, F: a nucleic acid number calculating step, G: an outputting step, H: a recording step, I: a nucleic acid extracting step, and J: an enzyme deactivating step. As needed, the method may include A2: estimating the number of nucleic acids contained in the cell suspension in A: the cell suspension producing step, and C1: an operation for observing cells before discharging and C3: an operation for counting cells after landing in C: the cell number counting step.

<Cell Suspension Producing Step>

The cell suspension producing step is a step of producing a cell suspension containing a plurality of cells including a nucleic acid having a specific base sequence, and a solvent.

The solvent means a liquid used for dispersing cells.

Suspension in the cell suspension means a state of cells being present dispersedly in the solvent.

Producing means a producing operation.

—Cell Suspension—

The cell suspension contains a plurality of cells including a nucleic acid having a specific base sequence, and a solvent, and further contains other components as needed.

——Cells——

The cells include a nucleic acid having a specific base sequence and are present in a plural number.

A cell means a structural, functional unit that forms an organism.

The cells are not particularly limited and may be appropriately selected depending on the intended purpose. All kinds of cells can be used regardless of whether the cells are eukaryotic cells, prokaryotic cells, multicellular organism cells, and unicellular organism cells. One of these kinds of cells may be used alone or two or more of these kinds of cells may be used in combination.

The eukaryotic cells are not particularly limited and may be appropriately selected depending on the intended purpose. Examples of the eukaryotic cells include animal cells, insect cells, plant cells, fungi, algae, and protozoans. One of these kinds of eukaryotic cells may be used alone or two or more of these kinds of eukaryotic cells may be used in combination. Among these kinds of eukaryotic cells, animal cells and fungi are preferable.

Adherent cells may be primary cells directly taken from tissues or organs, or may be cells obtained by passaging primary cells directly taken from tissues or organs a few times. Adherent cells may be appropriately selected depending on the intended purpose. Examples of adherent cells include differentiated cells and undifferentiated cells.

Differentiated cells are not particularly limited and may be appropriately selected depending on the intended purpose. Examples of differentiated cells include: hepatocytes, which are parenchymal cells of a liver; stellate cells; Kupffer cells; endothelial cells such as vascular endothelial cells, sinusoidal endothelial cells, and corneal endothelial cells; fibroblasts; osteoblasts; osteoclasts; periodontal ligament-derived cells; epidermal cells such as epidermal keratinocytes; epithelial cells such as tracheal epithelial cells, intestinal epithelial cells, cervical epithelial cells, and corneal epithelial cells; mammary glandular cells; pericytes; muscle cells such as smooth muscle cells and myocardial cells; renal cells; pancreatic islet cells; nerve cells such as peripheral nerve cells and optic nerve cells; chondrocytes; and bone cells.

Undifferentiated cells are not particularly limited and may be appropriately selected depending on the intended purpose. Examples of undifferentiated cells include: pluripotent stem cells such as embryonic stem cells, which are undifferentiated cells, mesenchymal stem cells having pluripotency; unipotent stem cells such as vascular endothelial progenitor cells having unipotency; and iPS cells.

Fungi are not particularly limited and may be appropriately selected depending on the intended purpose. Examples of fungi include molds and yeast fungi. One of these kinds of fungi may be used alone or two or more of these kinds of fungi may be used in combination. Among these kinds of fungi, yeast fungi are preferable because the cell cycles are adjustable and monoploids can be used.

The cell cycle means a cell proliferation process in which cells undergo cell division and cells (daughter cells) generated by the cell division become cells (mother cells) that undergo another cell division to generate new daughter cells.

Yeast fungi are not particularly limited and may be appropriately selected depending on the intended purpose. Bar1-deficient yeasts with enhanced sensitivity to a pheromone (sex hormone) that controls the cell cycle at a G1 phase are preferable. When yeast fungi are Bar1-deficient yeasts, the abundance ratio of yeast fungi with uncontrolled cell cycles can be reduced. This makes it possible to, for example, prevent the nucleic acid having a specific base sequence from increasing in number in the cells contained in a cell container (for example, a well plate, a microplate, and a microtiter plate).

The prokaryotic cells are not particularly limited and may be appropriately selected depending on the intended purpose. Examples of the prokaryotic cells include eubacteria and archaea. One of these kinds of prokaryotic cells may be used alone or two or more of these kinds of prokaryotic cells may be used in combination.

As the cells, dead cells are preferable. With dead cells, it is possible to prevent occurrence of cell division after fractionation.

As the cells, cells that can emit light upon reception of light are preferable. With cells that can emit light upon reception of light, it is possible to land the cells on a cell contained base while having a highly accurate control on the number of cells.

Reception of light means receiving of light.

An optical sensor means a passive sensor configured to collect, with a lens, any light in the range from visible light rays visible by human eyes to near infrared rays, short-wavelength infrared rays, and thermal infrared rays that have longer wavelengths than the visible light rays, to obtain, for example, shapes of target cells in the form of image data.

——Cells that can Emit Light Upon Reception of Light——

The cells that can emit light upon reception of light are not particularly limited and may be appropriately selected depending on the intended purpose so long as the cells can emit light upon reception of light. Examples of the cells include cells stained with a fluorescent dye, cells expressing a fluorescent protein, and cells labeled with a fluorescent-labeled antibody.

A cellular site stained with a fluorescent dye, expressing a fluorescent protein, or labeled with a fluorescent-labeled antibody is not particularly limited. Examples of the cellular site include a whole cell, a cell nucleus, and a cellular membrane.

——Fluorescent dye——

Examples of the fluorescent dye include fluoresceins, azo dyes, rhodamines, coumarins, pyrenes, cyanines. One of these fluorescent dyes may be used alone or two or more of these fluorescent dyes may be used in combination. Among these fluorescent dyes, fluoresceins, azo dyes, and rhodamines are preferable, and eosin, Evans blue, trypan blue, rhodamine 6G, rhodamine B, and rhodamine 123 are more preferable.

As the fluorescent dye, a commercially available product may be used. Examples of the commercially available product include product name: EOSIN Y (available from Wako Pure Chemical Industries, Ltd.), product name: EVANS BLUE (available from Wako Pure Chemical Industries, Ltd.), product name: TRYPAN BLUE (available from Wako Pure Chemical Industries, Ltd.), product name: RHODAMINE 6G (available from Wako Pure Chemical Industries, Ltd.), product name: RHODAMINE B (available from Wako Pure Chemical Industries, Ltd.), and product name: RHODAMINE 123 (available from Wako Pure Chemical Industries, Ltd.).

——Fluorescent Protein——

Examples of the fluorescent protein include Sirius, EBFP, ECFP, mTurquoise, TagCFP, AmCyan, mTFP1, Midoriishi-Cyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. One of these fluorescent proteins may be used alone or two or more of these fluorescent proteins may be used in combination.

——Fluorescent-Labeled Antibody——

The fluorescent-labeled antibody is not particularly limited and may be appropriately selected depending on the intended purpose so long as the fluorescent-labeled antibody is fluorescent-labeled. Examples of the fluorescent-labeled antibody include CD4-FITC and CD8-PE. One of these fluorescent-labeled antibodies may be used alone or two or more of these fluorescent-labeled antibodies may be used in combination.

[Method for Producing Cell Suspension that can Emit Light Upon Reception of Light]

In an Erlenmeyer flask, a 90 mL fraction of a gene recombinant yeast cultured in, for example, 50 g/L of a YPD medium (e.g., product name: YPD MEDIUM available from Clontech Laboratories, Inc.) is mixed with 900 microliters of a factor (available from Sigma-Aldrich Co., LLC, α1-MATING FACTOR ACETATE SALT) prepared to 500 micrograms/mL with a Dulbecco's phosphate buffered saline (e.g., available from Thermo Fisher Scientific Inc., hereinafter may also be referred to as "DPBS") and incubated with a bioshaker (e.g., a device name: BR-23FH, available from Taitec Corporation) at a shaking speed of 250 rpm at a temperature of 28 degrees C. for 2 hours, to synchronize the yeast at a G0/G1 phase, to obtain a yeast suspension.

Forty-five milliliters of the synchronization-confirmed yeast suspension is transferred to a centrifuge tube (e.g., VIOLAMO, product name: VIO-50R, available from As One Corporation) and centrifuged with a centrifugal separator (e.g., device name: CF16RN, available from Hitachi, Ltd.) at a rotation speed of 3,000 rpm for 5 minutes, with subsequent supernatant removal, to obtain yeast pellets. Four milliliters of formalin (e.g., available from Wako Pure Chemical Industries, Ltd., 062-01661) is added to the yeast pellets, and the resultant is left to stand still for 5 minutes, then centrifuged with subsequent supernatant removal, and suspended with addition of 10 mL of ethanol, to obtain an immobilized yeast suspension.

Five hundred microliters of the immobilized yeast suspension is transferred to a 1.5 mL light-shielding tube (e.g., available from Watson, 131-915BR), centrifuged with a centrifugal separator at a rotation speed of 3,000 rpm for 5 minutes with subsequent supernatant removal, suspended sufficiently by pipetting with addition of 400 microliters of DPBS (1 mM EDTA) prepared to 1 mM EDTA (e.g., available from Tocris Bioscience, 200-449-4), then centrifuged with a centrifugal separator at a rotation speed of 3,000 rpm for 5 minutes with subsequent supernatant removal, to obtain yeast pellets. One milliliter of an Evans blue aqueous solution (e.g., available from Wako Pure Chemical Industries, Ltd., 054-04061) prepared to 1 mg/mL is added to the pellets, and the resultant is stirred with a vortex for 5 minutes, then centrifuged with a centrifugal separator at a rotation speed of 3,000 rpm for 5 minutes with subsequent supernatant removal, and stirred with a vortex with addition of DPBS (1 mM EDTA), to obtain a stained yeast suspension.

The volume average particle diameter of the cells is preferably 100 micrometers or less, more preferably 50 micrometers or less, and particularly preferably 20 micrometers or less in a free state. When the volume average particle diameter of the cells is 100 micrometers or less, the cells can be suitably used in an inkjet method.

The volume average particle diameter of the cells can be measured by, for example, a measuring method described below.

Ten microliters is extracted from the produced stained yeast dispersion liquid and poured onto a plastic slide formed of PMMA. Then, with an automated cell counter (product name: COUNTESS AUTOMATED CELL COUNTER, available from Invitrogen), the volume average particle diameter of the cells can be measured. The cell number can be obtained by a similar measuring method.

The concentration of the cells in the cell suspension is not particularly limited, may be appropriately selected depending on the intended purpose, and is preferably $5 \times 10^4$ cells/mL or higher but $5 \times 10^8$ cells/mL or lower and more preferably $5 \times 10^4$ cells/mL or higher but $5 \times 10^7$ cells/mL or lower. When the cell number is $5 \times 10^4$ cells/mL or higher but $5 \times 10^8$ cells/mL or lower, it can be ensured that cells be contained in a discharged liquid droplet without fail. The cell number can be measured with an automated cell counter (product name: COUNTESS AUTOMATED CELL COUNTER, available from Invitrogen) in the same manner as measuring the volume average particle diameter.

The cell number of cells including a nucleic acid having a specific base sequence is not particularly limited and may be appropriately selected depending on the intended purpose so long as the cell number is a plural number.

————Nucleic Acid Having Specific Base Sequence————

The nucleic acid having a specific base sequence is not particularly limited and may be appropriately selected depending on the intended purpose. Examples of the nucleic acid having a specific base sequence include base sequences used in infectious disease testing, naturally non-existent nucleic acids, animal cell-derived base sequences, and plant cell-derived base sequences. One of these nucleic acids may be used alone or two or more of these nucleic acids may be used in combination. As the nucleic acid having a specific base sequence, plasmids can also be suitably used.

The term "specific" means "particularly specified".

A nucleic acid means a polymeric organic compound in which a nitrogen-containing base derived from purine or pyrimidine, sugar, and phosphoric acid are bonded with one another regularly.

The nucleic acid having a specific base sequence is not particularly limited and may be appropriately selected depending on the intended purpose. Examples of the specific nucleic acid include DNA and RNA. Among these specific nucleic acids, DNA corresponding to RNA derived from a region to which an infectious disease such as norovirus is immobilized, and naturally non-existent DNA can be suitably used.

The nucleic acid of the plurality of cells including a nucleic acid having a specific base sequence may be a nucleic acid having a specific base sequence derived from the cells to be used or may be a nucleic acid having a specific base sequence introduced by transgenesis. When a nucleic acid having a specific base sequence introduced by transgenesis and a plasmid are used as the nucleic acid having a specific base sequence, it is preferable to confirm that 1 copy of the nucleic acid having a specific base sequence is introduced per cell. The method for confirming that 1 copy of the nucleic acid having a specific base sequence is introduced is not particularly limited and may be appropriately selected depending on the intended purpose. Examples of the method include confirming methods using a sequencer, a PCR method, and a Southern blotting method.

The method for transgenesis is not particularly limited and may be appropriately selected depending on the intended purpose, so long as the method can introduce an intended number of molecules of the nucleic acid having a specific base sequence at an intended position. Examples of the method include homologous recombination, CRISPR/Cas9, TALEN, Zinc finger nuclease, Flip-in, and Jump-in. Particularly, in the case of yeast fungi, homologous recombination is preferable in terms of a high efficiency and ease of controlling.

[Method for Producing Gene Recombinant Yeast]

For producing a recombinant, a budding yeast can be used as a carrier cell for 1 copy of a specific base sequence. Specifically, using a sequence specific to norovirus as a specific base sequence, a recombinant yeast can be produced by producing the specific base sequence in a tandem arrangement with a selectable marker, and introducing 1 copy of the specific base sequence into a yeast chromosome by homologous recombination, targeting, for example, a BAR1 region of the carrier cell.

Examples of the budding yeast include W303-1A (product name: ATCC4001408, available from ATCC).

The sequence specific to norovirus is available from, for example, NCBI (National Center for Biotechnology Information, for example, see Sequence No. 1).

Examples of the selectable marker include a uracil synthesis enzyme (e.g., URA3), a histidine synthesis enzyme (e.g., HIS3), a tryptophan synthesis enzyme (e.g., TRP1), a lysine synthesis enzyme (e.g., LYS2), a methionine synthesis enzyme (e.g., MET17), and an adenine synthesis enzyme (e.g., ADE2).

——Solvent——

The solvent is not particularly limited and may be appropriately selected depending on the intended purpose. Examples of the solvent include water, a culture fluid, a separation liquid, a diluent, a buffer, an organic matter dissolving liquid, an organic solvent, a polymeric gel solution, a colloid dispersion liquid, an electrolytic aqueous solution, an inorganic salt aqueous solution, a metal aqueous solution, and a mixture liquids of these liquids. One of these solvents may be used alone or two or more of these solvents may be used in combination. Among these solvents, water and a buffer are preferable, and water, a phosphate buffered saline (PBS), and a Tris-EDTA buffer (TE) are more preferable.

——Additive——

An additive is not particularly limited and may be appropriately selected depending on the intended purpose. Examples of the additive include a surfactant, a nucleic acid, and a resin. One of these additives may be used alone or two or more of these additives may be used in combination.

———Surfactant———

A surfactant can prevent mutual aggregation of cells and improve continuous discharging stability.

The surfactant is not particularly limited and may be appropriately selected depending on the intended purpose. Examples of the surfactant include ionic surfactants and nonionic surfactants. One of these surfactants may be used alone or two or more of these surfactants may be used in combination. Among these surfactants, nonionic surfactants are preferable because proteins are neither modified nor deactivated by nonionic surfactants, although depending on the addition amount of the nonionic surfactants.

Examples of the ionic surfactants include fatty acid sodium, fatty acid potassium, alpha-sulfo fatty acid ester sodium, sodium straight-chain alkyl benzene sulfonate, alkyl sulfuric acid ester sodium, alkyl ether sulfuric acid ester sodium, and sodium alpha-olefin sulfonate. One of these ionic surfactants may be used alone or two or more of these ionic surfactants may be used in combination. Among these ionic surfactants, fatty acid sodium is preferable and sodium dodecyl sulfonate (SDS) is more preferable.

Examples of the nonionic surfactants include alkyl glycoside, alkyl polyoxyethylene ether (e.g., BRIJ series), octyl phenol ethoxylate (e.g., TRITON X series, IGEPAL CA series, NONIDET P series, and NIKKOL OP series), polysorbates (e.g., TWEEN series such as TWEEN 20), sorbitan fatty acid esters, polyoxyethylene fatty acid esters, alkyl maltoside, sucrose fatty acid esters, glycoside fatty acid esters, glycerin fatty acid esters, propylene glycol fatty acid esters, and fatty acid monoglyceride. One of these nonionic surfactants may be used alone or two or more of these nonionic surfactants may be used in combination. Among these nonionic surfactants, polysorbates are preferable.

The content of the surfactant is not particularly limited, may be appropriately selected depending on the intended purpose, and is preferably 0.001% by mass or greater but 30% by mass or less relative to the total amount of the cell suspension. When the content of the surfactant is 0.001% by mass or greater, an effect of adding the surfactant can be obtained. When the content of the surfactant is 30% by mass or less, aggregation of cells can be suppressed, making it possible to strictly control the number of nucleic acid molecules in the cell suspension.

———Nucleic Acid———

The nucleic acid is not particularly limited and may be appropriately selected depending on the intended purpose so long as the nucleic acid does not affect detection of the nucleic acid having a specific base sequence. Examples of the nucleic acid include ColE1 DNA. With such a nucleic acid, it is possible to prevent the nucleic acid having a specific base sequence from adhering to the wall surface of the cell contained base.

———Resin———

The resin is not particularly limited and may be appropriately selected depending on the intended purpose. Examples of the resin include polyethyleneimine.

——Other Materials——

Other materials are not particularly limited and may be appropriately selected depending on the intended purpose. Examples of the other materials include a cross-linking agent, a pH adjustor, an antiseptic, an antioxidant, an osmotic pressure regulator, a humectic, and a dispersant.

[Method for Dispersing Cells]

The method for dispersing the cells is not particularly limited and may be appropriately selected depending on the intended purpose. Examples of the method include a medium method such as a bead mill, an ultrasonic method such as an ultrasonic homogenizer, and a method using a pressure difference such as a French press. One of these methods may be used alone or two or more of these methods may be used in combination. Among these methods, the ultrasonic method is more preferable because the ultrasonic method has low damage on the cells. With the medium method, a high crushing force may destroy cellular membranes or cell walls, and the medium may mix as contamination.

[Method for Screening Cells]

The method for screening the cells is not particularly limited and may be appropriately selected depending on the intended purpose. Examples of the method include screening by wet classification, a cell sorter, and a filter. One of these methods may be used alone or two or more of these methods may be used in combination. Among these methods, screening by a cell sorter and a filter is preferable because the method has low damage on the cells.

It is preferable to measure the cell cycles of the cells contained in the cell suspension, then based on the measured cell cycles, estimate the number of nucleic acids having a specific base sequence from the cell number contained in the cell suspension, and calculate the number of nucleic acids having a specific base sequence located in each cell contained region based on the estimated number of nucleic acids having a specific base sequence.

Measuring the cell cycles means quantifying nuclear phases of cells due to cell division.

Estimating the number of nucleic acids means estimating the copy number of the nucleic acid based on the cell number and the measured cell cycles.

What is to be counted needs not be the cell number, but may be the number of specific base sequences. Typically, it is safe to consider that the number of specific base sequences is equal to the cell number, because the cells to be selected as the cells to be counted are cells each including 1 specific base sequence (=1 specific base sequence per cell), or because 1 specific base sequence is introduced per cell by gene recombination. However, nucleic acid replication occurs in cells in order for the cells to undergo cell division at specific cycles. Cell cycles are different depending on the kinds of cells. By extracting a predetermined amount of the solution from the cell suspension and measuring the cycles of a plurality of cells, it is possible to calculate an expected value of the number of nucleic acids having a specific base sequence included in 1 cell and the degree of certainty of the estimated value. This can be realized by observing nuclear stained cells with a flow cytometer.

Degree of certainty means a probability of occurrence of 1 specific event, predicted beforehand, when there are possibilities of occurrence of some events.

Calculation means deriving a needed value by a calculating operation.

Figure 2:
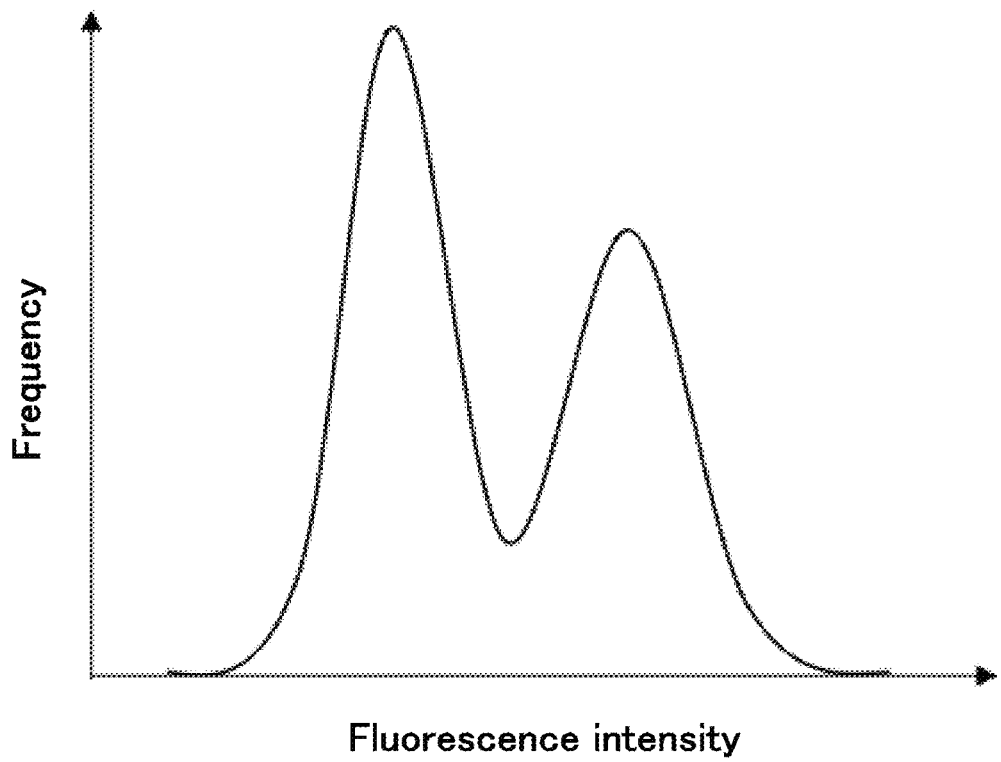
FIG. 2 is a graph plotting an example of a relationship between the frequency and the fluorescence intensity of cells in which DNA replication has occurred.

FIG. 2 is a graph plotting an example of a relationship between the frequency and the fluorescence intensity of cells in which DNA replication has occurred. As plotted in FIG. 2, based on presence or absence of DNA replication, 2 peaks appear on the histogram. Hence, the percentage of presence of cells in which DNA replication has occurred can be calculated. Based on this calculation result, the average DNA number included in 1 cell can be calculated. The number of nucleic acids can be estimated by multiplying the counted cell number by the obtained average DNA number.

It is preferable to perform an operation of controlling the cell cycles before producing the cell suspension. By preparing the cells uniformly to a state before replication occurs or a state after replication occurs, it is possible to calculate the number of nucleic acids having a specific base sequence based on the cell number more accurately.

It is preferable to calculate a degree of certainty (probability) for the estimated number of nucleic acids. By calculating a degree of certainty (probability), it is possible to express and output the degree of certainty as a variance or a standard deviation based on these values. When adding up influences of a plurality of factors, it is possible use a square root of the sum of the squares of the standard deviation commonly used. For example, a correct answer percentage for the number of cells discharged, the number of DNA in a cell, and a landing ratio at which discharged cells land in cell contained regions can be used as the factors. A highly influential factor may be selected for calculation.

<Liquid Droplet Discharging Step>

The liquid droplet discharging step is a step of discharging the cell suspension in the form of liquid droplets with a liquid droplet discharging unit onto a base including at least one cell contained region.

A liquid droplet means a gathering of a liquid formed by a surface tension.

Discharging means making the cell suspension fly in the form of liquid droplets.

A base means a material including a cell contained region capable of containing a cell.

A cell contained region means a specific region capable of containing a cell.

As a liquid droplet discharging unit, a unit configured to discharge the cell suspension in the form of liquid droplets (hereinafter may also be referred to as "discharging head") can be suitably used.

Examples of the method for discharging the cell suspension in the form of liquid droplets include an on-demand method and a continuous method. Of these methods, in the case of the continuous method, there is a tendency that the dead volume of the cell suspension used is high, because of, for example, empty discharging until the discharging state becomes stable, adjustment of the amount of liquid droplets, and continued formation of liquid droplets even during transfer between the cell contained regions. In the present disclosure, in terms of cell number adjustment, it is preferable to suppress influence due to the dead volume. Hence, of the two methods, the on-demand method is more preferable.

Examples of the on-demand method include a plurality of known methods such as a pressure applying method of applying a pressure to a liquid to discharge the liquid, a thermal method of discharging a liquid by film boiling due to heating, and an electrostatic method of drawing liquid droplets by electrostatic attraction to form liquid droplets. Among these methods, the pressure applying method is preferable for the reason described below.

In the electrostatic method, there is a need for disposing an electrode in a manner to face a discharging unit that is configured to retain the cell suspension and form liquid droplets. In the method for producing a cell contained base of the present disclosure, the cell contained base for receiving liquid droplets is disposed at the facing position. Hence, it is preferable not to provide an electrode, in order to increase the degree of latitude in the cell contained base configuration.

In the thermal method, there are a risk of local heating concentration that may affect the cells, which are a biomaterial, and a risk of kogation to the heater portion. Influences by heat depend on the components contained or the purpose for which the cell contained base is used. Therefore, there is no need for flatly rejecting the thermal method. However, the pressure applying method is preferable because the pressure applying method has a lower risk of kogation to the heater portion than the thermal method.

Examples of the pressure applying method include a method of applying a pressure to a liquid using a piezo element, and a method of applying a pressure using a valve such as an electromagnetic valve. The configuration example of a liquid droplet generating device usable for discharging liquid droplets of the cell suspension is illustrated in FIG. 3A to FIG. 3C.

Figure 3A:
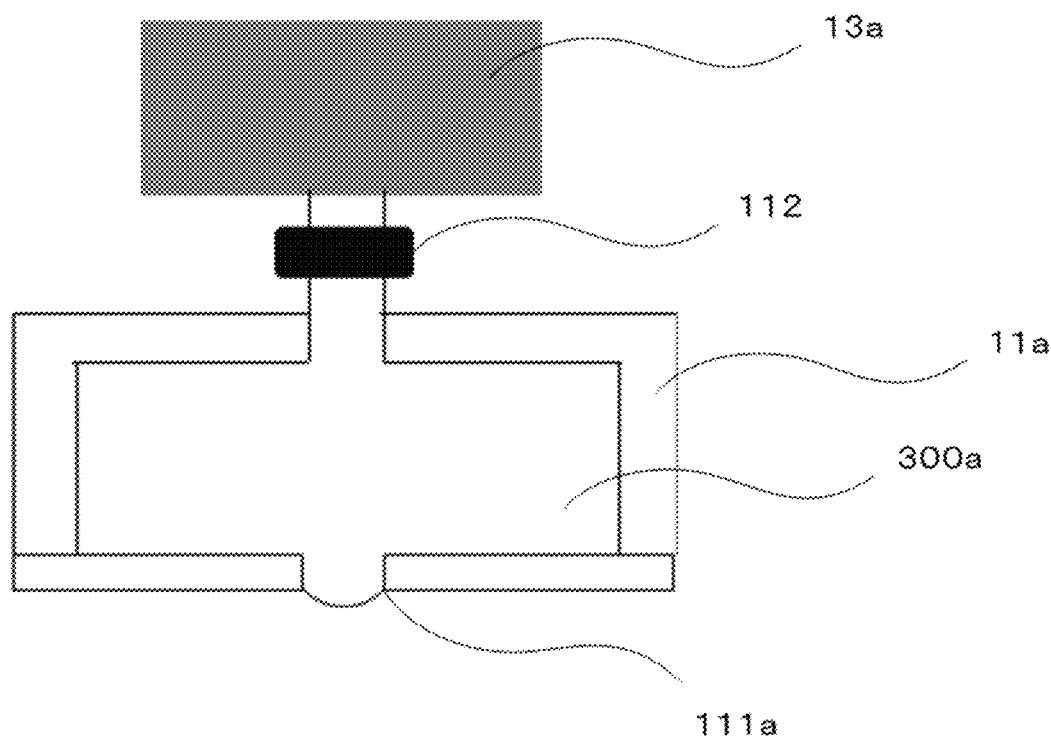
FIG. 3A is an exemplary diagram illustrating an example of an electromagnetic valve-type discharging head.

FIG. 3A is an exemplary diagram illustrating an example of an electromagnetic valve-type discharging head. The electromagnetic valve-type discharging head includes an electric motor $13a$, an electromagnetic valve 2, a liquid chamber $11a$, a cell suspension $300a$, and a nozzle $111a$.

As the electromagnetic valve-type discharging head, for example, a dispenser available from Tech Elan LLC can be suitably used.

Figure 3B:
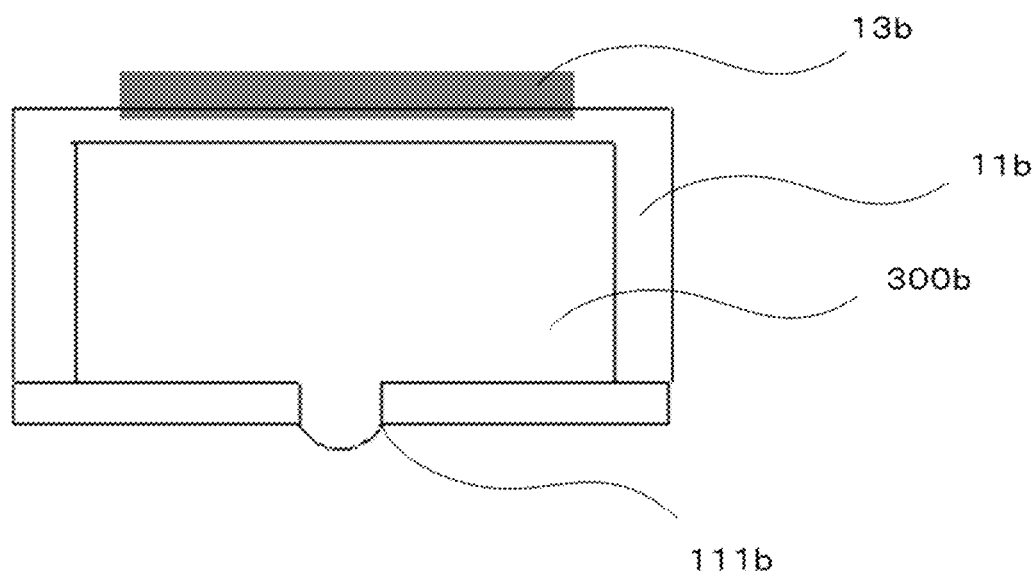
FIG. 3B is an exemplary diagram illustrating an example of a piezo-type discharging head.
Figure 3C:
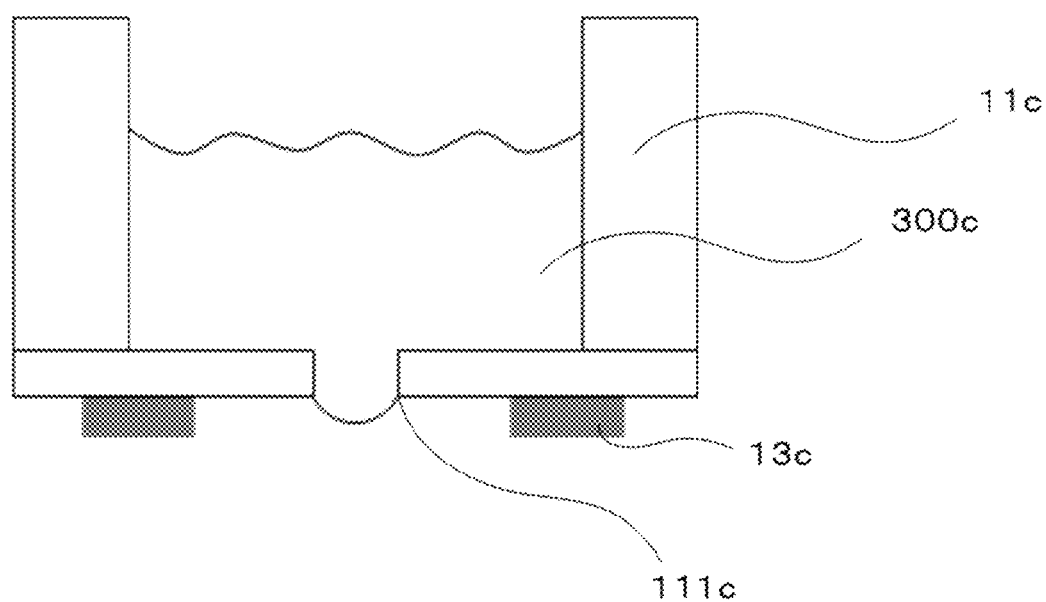
FIG. 3C is an exemplary diagram of a modified example of the piezo-type discharging head illustrated in FIG. 3B.

FIG. 3B is an exemplary diagram illustrating an example of a piezo-type discharging head. The piezo-type discharging head includes a piezoelectric element $13b$, a liquid chamber $11b$, a cell suspension $300b$, and a nozzle $111b$.

As the piezo-type discharging head, for example, a single cell printer available from Cytena GmbH can be suitably used.

Any of these discharging heads may be used. However, the pressure applying method by the electromagnetic valve is not capable of forming liquid droplets at a high speed repeatedly. Therefore, it is preferable to use the piezo method in order to increase the throughput of producing the cell contained base. A piezo-type discharging head using a common piezoelectric element $13b$ may cause unevenness in the cell concentration due to settlement, or may have nozzle clogging.

Therefore, a more preferable configuration is the configuration illustrated in FIG. 3C. FIG. 3C is an exemplary diagram of a modified example of a piezo-type discharging head using the piezoelectric element illustrated in FIG. 3B.

The discharging head of FIG. 3C includes a piezoelectric element 13c, a liquid chamber 11c, a cell suspension 300c, and a nozzle 111c.

In the discharging head of FIG. 3C, when a voltage is applied to the piezoelectric element 13c from an unillustrated control device, a compressive stress is applied in the horizontal direction of the drawing sheet. This can deform the membrane in the upward-downward direction of the drawing sheet. As a result, liquid droplets are formed while the cell suspension 300c in the liquid chamber 11c is being stirred. This makes it possible to suppress nozzle clogging and form liquid droplets at a high speed repeatedly.

Examples of any other method than the on-demand method include a continuous method for continuously forming liquid droplets. When pushing out liquid droplets by pressurization, the continuous method applies regular fluctuations using a piezoelectric element or a heater, to make it possible to continuously form minute liquid droplets. Further, the continuous method can select whether to land a flying liquid droplet into a cell contained region or to recover the liquid droplet in a recovery unit, by controlling the discharging direction of the liquid droplet with voltage application. Such a method is employed in a cell sorter or a flow cytometer. For example, a device named: CELL SORTER SH800 available from Sony Corporation can be used.

Figure 4A:
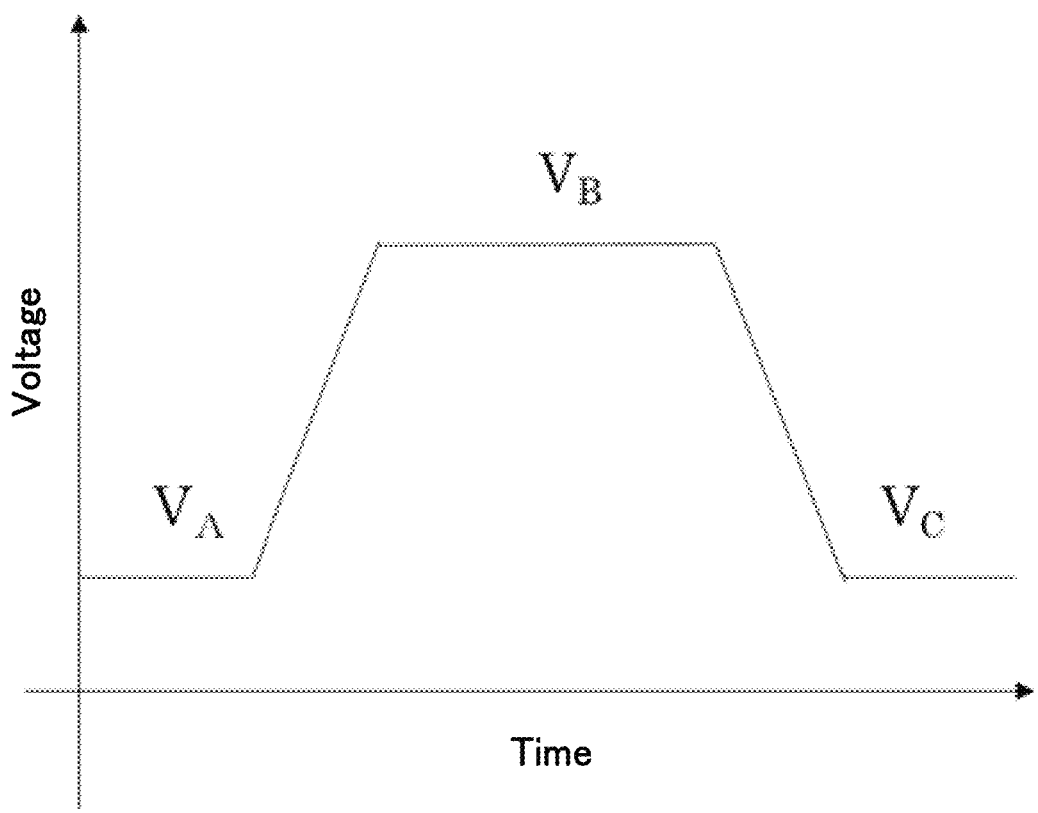
FIG. 4A is an exemplary graph plotting an example of a voltage applied to a piezoelectric element.
Figure 4B:
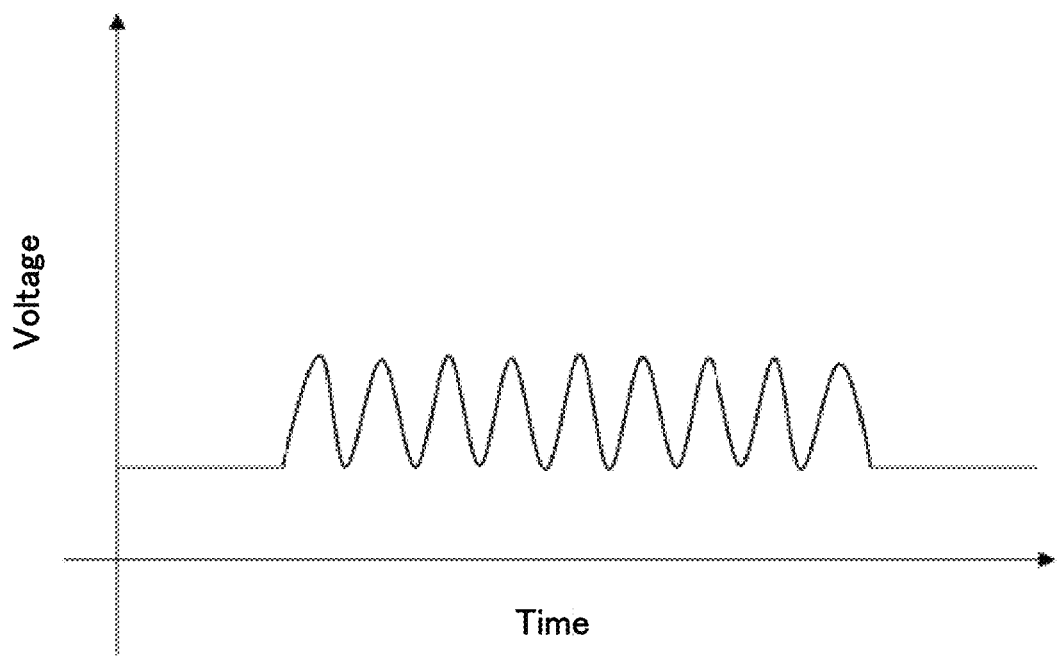
FIG. 4B is an exemplary graph plotting another example of a voltage applied to a piezoelectric element.

FIG. 4A is an exemplary graph plotting an example of a voltage applied to a piezoelectric element. FIG. 4B is an exemplary graph plotting another example of a voltage applied to a piezoelectric element. FIG. 4A plots a drive voltage for forming liquid droplets. Depending on the high or low level of the voltage ($V_A$, $V_B$, and $V_C$), it is possible to form liquid droplets. FIG. 4B plots a voltage for stirring the cell suspension without discharging liquid droplets.

During a period in which liquid droplets are not discharged, inputting a plurality of pulses that are not high enough to discharge liquid droplets enables the cell suspension in the liquid chamber to be stirred, making it possible to suppress occurrence of a concentration distribution due to settlement of the cells.

The liquid droplet forming operation of the discharging head that can be used in the present disclosure will be described below.

Figure 5A:
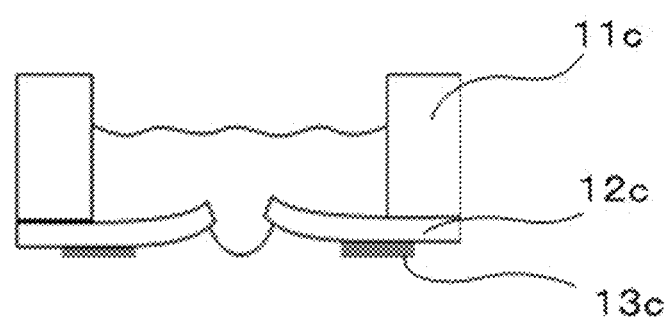
FIG. 5A is an exemplary diagram illustrating an example of a liquid droplet state.
Figure 5B:
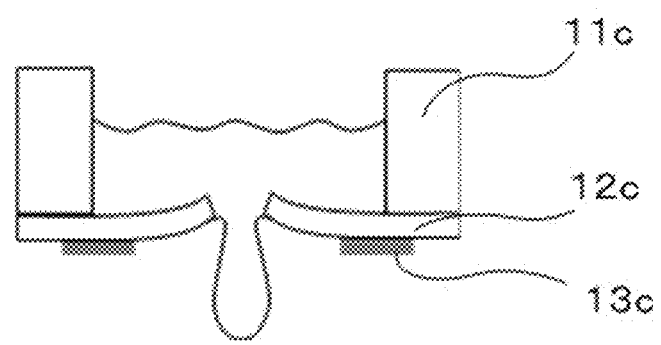
FIG. 5B is an exemplary diagram illustrating an example of a liquid droplet state.
Figure 5C:
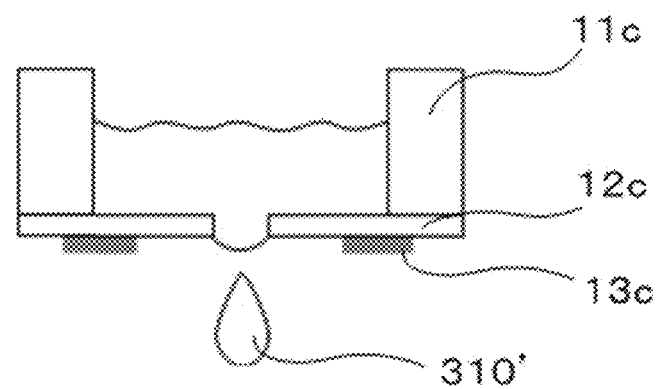
FIG. 5C is an exemplary diagram illustrating an example of a liquid droplet state.

The discharging head can discharge liquid droplets with application of a pulsed voltage to the upper and lower electrodes formed on the piezoelectric element. FIG. 5A to FIG. 5C are exemplary diagrams illustrating liquid droplet states at the respective timings. In FIG. 5A, first, upon application of a voltage to the piezoelectric element 13c, a membrane 12c abruptly deforms to cause a high pressure between the cell suspension retained in the liquid chamber 11c and the membrane 12c. This pressure pushes out a liquid droplet outward through the nozzle portion. Next, as illustrated in FIG. 5B, for a period of time until when the pressure relaxes upward, the liquid is continuously pushed out through the nozzle portion, to grow the liquid droplet. Finally, as illustrated in FIG. 5C, when the membrane 12c returns to the original state, the liquid pressure about the interface between the cell suspension and the membrane 12c lowers, to form a liquid droplet 310'.

The base is not particularly limited so long as the base is a component commonly used in bio fields. Examples of the base include: plates provided with at least any one kind of sections selected from the group consisting of holes, concaves, and convexes; plates provided with no sections; and tubes. More specifically, examples of plates provided with sections include 24-well, 96-well, and 384-well plates, examples of plates provided with no sections include glass slides, and examples of tubes include 8-series PCR tubes and PCR tubes used alone.

The cell contained region is not particularly limited and may be appropriately selected depending on the intended purpose, so long as the cell contained region has a specific region capable of containing a cell. Examples of the cell contained region include sections provided on a cell contained base, and regions provided on a cell contained base other than sections. More specific examples of the cell contained region include wells in a 24-well, 96-well, and 384-well plates.

The number of cell contained regions in the base is not particularly limited and may be appropriately selected depending on the intended purpose. The number of cell contained regions may be a single number or a plural number. Here, the number of cell contained regions means the number of sections in the case of a plate provided with sections, means the number of specific regions capable of containing a cell in the case of a plate provided with no sections, and means the number of tubes in the case of a tube.

As a base with a plural number of cell contained regions, it is preferable to use bases in which 24, 96, 384, or such a number of cell contained regions as commonly used in the industry are formed with dimensions commonly used in the industry.

In the present disclosure, a base may be referred to as plate. In the present disclosure, when a base is referred to as plate, the plate means at least any one base selected from the group consisting of a base including concaves and convexes and a base free of concaves and convexes.

The material of the base is not particularly limited and may be appropriately selected depending on the intended purpose. In consideration of a post-treatment, it is preferable to use a material that suppresses adhesion of cells and nucleic acids to wall surfaces.

As the base, it is preferable to use a base provided with a recognition unit allowing recognition of each base. As the recognition unit, for example, a barcode, a QR code (registered trademark), a Radio Frequency Identifier (hereinafter may also be referred to as "RFID") can be used. In mass production of cell contained bases, RFID that can be used wirelessly is preferable.

As the base, it is preferable to use a 1-well microtube, an 8-series tube, a 96-well plate, and 384-well plate. When the number of cell contained regions are a plural number, it is possible to dispense the same number of cells into the cell contained regions of these bases, or it is also possible to dispense numbers of cells of different levels into the cell contained regions. There may be a cell contained region in which no cells are contained. Particularly, for producing a cell contained base used for evaluating a real-time PCR device or digital PCR device configured to quantitatively evaluate an amount of nucleic acids, it is preferable to dispense numbers of nucleic acids of a plurality of levels. For example, it is conceivable to produce a cell contained base into which cells (or nucleic acids) are dispensed at 7 levels, namely about 1 cell, 2 cells, 4 cells, 8 cells, 16 cells, 32 cells, and 64 cells. Using such a cell contained base, it is possible to inspect, for example, quantitativity, linearity, and lower limit of evaluation of a real-time PCR device or digital PCR device.

<Cell Number Counting Step>

The cell number counting step is a step of counting a number of cells contained in the liquid droplet with a plurality of sensors from two or more directions while the liquid droplet is flying into the cell contained region.

A sensor means a device configured to, by utilizing some scientific principles, change mechanical, electromagnetic, thermal, acoustic, or chemical properties of natural phenomena or artificial products or spatial information/temporal information indicated by these properties into signals, which are a different medium easily handleable by humans or machines.

Counting means counting of numbers.

The cell number counting step is not particularly limited and may be appropriately selected depending on the intended purpose, so long as the cell number counting step counts the number of cells contained in the liquid droplet with a plurality of sensors from two or more directions while the liquid droplet is flying into the cell contained region. The cell number counting step may include an operation for observing cells before discharging and an operation for counting cells after landing.

As a method for counting the number of cells contained in the liquid droplet while the liquid droplet is flying into the cell contained region, it is preferable to count the number of cells in the liquid droplet at a timing at which the liquid droplet is at a position that is immediately above a desired cell contained region and at which the liquid droplet is predicted to enter the cell contained region in the base without fail. When the cell contained regions have openings, the timing means a timing at which the liquid droplet is at a position immediately above the opening of a desired cell contained region.

Examples of the method for counting the number of cells in the liquid droplet include an optical detection method and an electric or electromagnetic detection method.

—Optical Detection Method—

Figure 7:
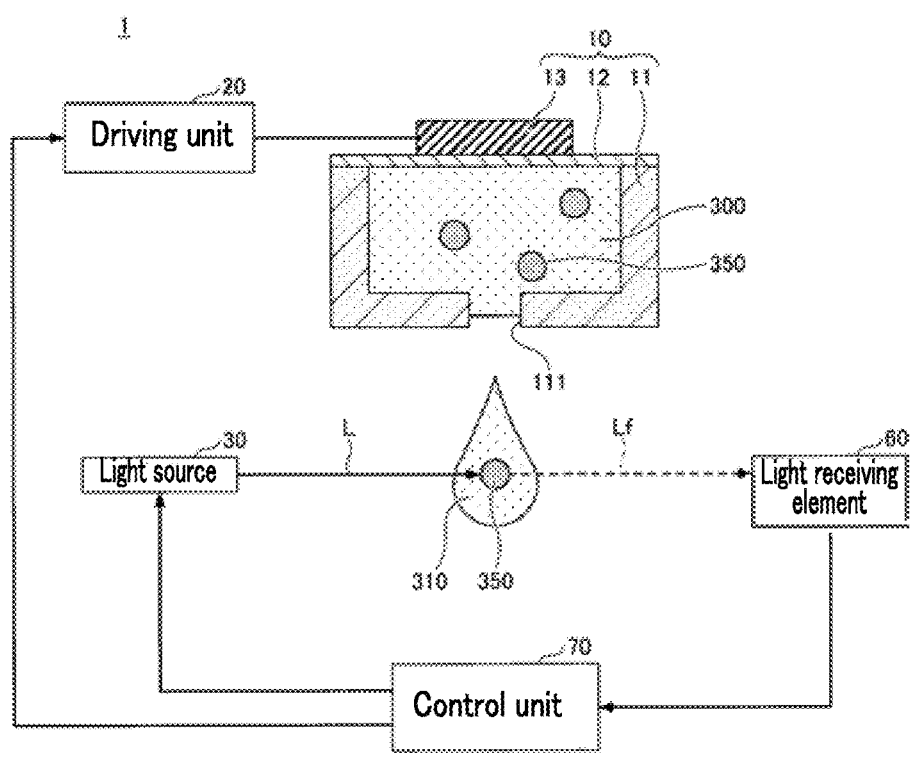
FIG. 7 is an exemplary diagram illustrating an example of a liquid droplet forming device.
Figure 11:
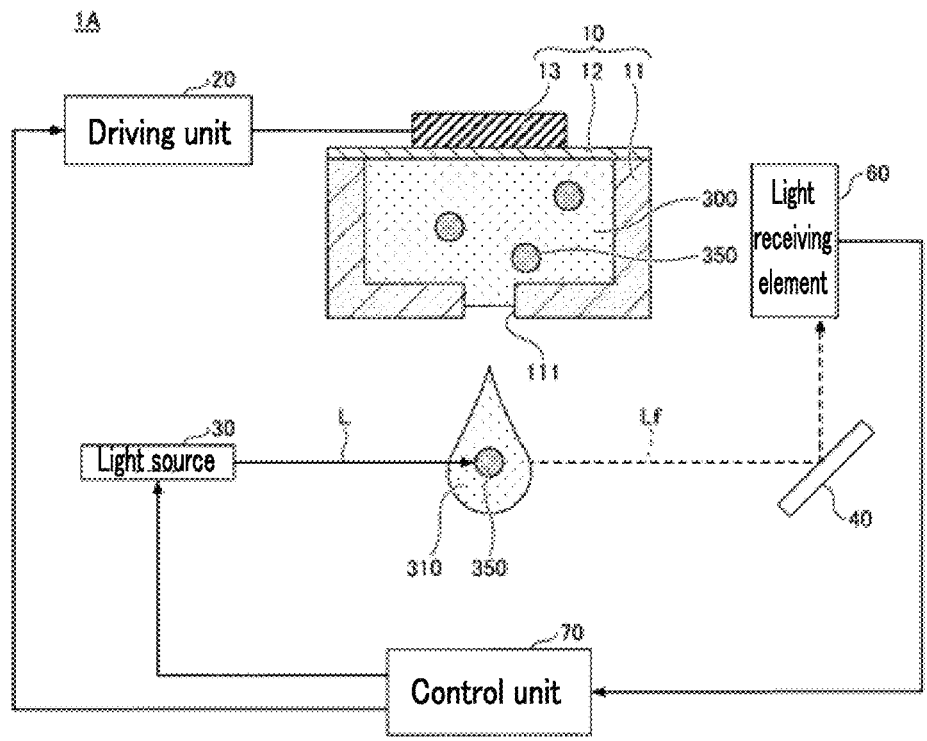
FIG. 11 is an exemplary diagram of a modified example of the liquid droplet forming device of FIG. 7.
Figure 12:
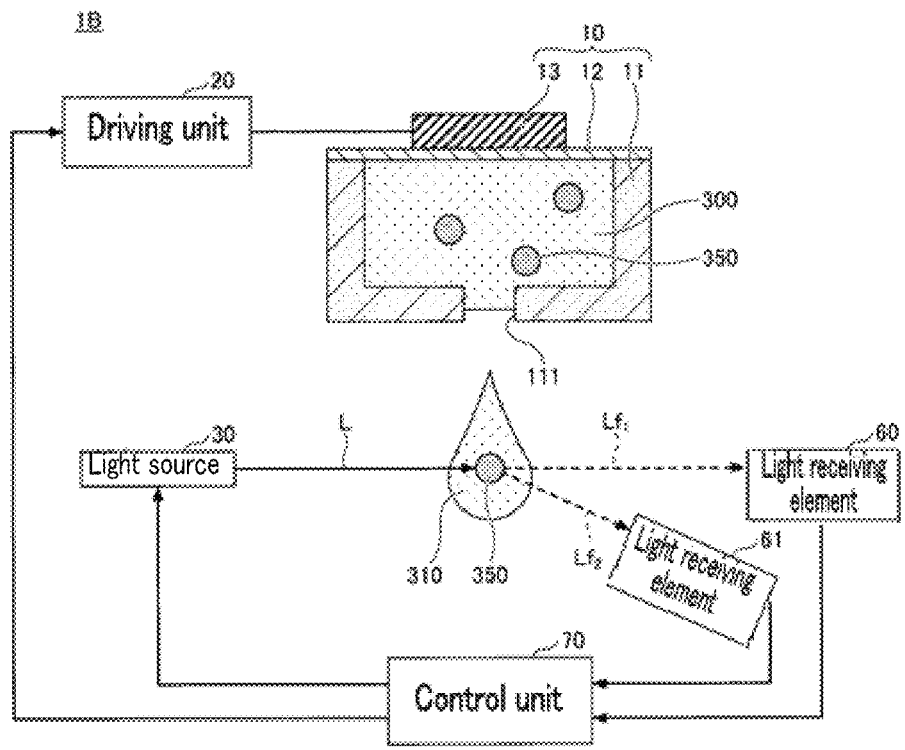
FIG. 12 is an exemplary diagram illustrating another modified example of the liquid droplet forming device of FIG. 7.

With reference to FIG. 7, FIG. 11, and FIG. 12, an optical detection method will be described below.

FIG. 7 is an exemplary diagram illustrating an example of a liquid droplet forming device. FIG. 11 and FIG. 12 are exemplary diagrams illustrating other examples of the liquid droplet forming device. As illustrated in FIG. 7, the liquid droplet forming device 1 includes a discharging head (liquid droplet discharging unit) 10, a driving unit 20, a light source 30, a light receiving element 60, and a control unit 70.

In FIG. 7, a liquid obtained by dispersing cells in a predetermined solution after fluorescently staining the cells with a specific pigment is used as the cell suspension. Cells are counted by irradiating the liquid droplets formed by the discharging head with light having a specific wavelength and emitted from the light source and detecting fluorescence emitted by the cells with the light receiving element. Here, autofluorescence emitted by molecules originally contained in the cells may be utilized, in addition to the method of staining the cells with a fluorescent pigment. Alternatively, genes for producing fluorescent proteins (for example, GFP (Green Fluorescent Proteins)) may be previously introduced into the cells, in order that the cells may emit fluorescence.

Irradiation of light means application of light.

The discharging head 10 includes a liquid chamber 11, a membrane 12, and a driving element 13 and can discharge a cell suspension 300 suspending fluorescent-stained cells 350 in the form of liquid droplets.

The liquid chamber 11 is a liquid retaining portion configured to retain the cell suspension 300 suspending the fluorescent-stained cells 350. A nozzle 111, which is a through-hole, is formed in the lower surface of the liquid chamber 11. The liquid chamber 11 may be formed of, for example, a metal, silicon, or a ceramic. Examples of the fluorescent-stained cells 350 include inorganic particles and organic polymer particles stained with a fluorescent pigment.

The membrane 12 is a film-shaped member secured on the upper end portion of the liquid chamber 11. The planar shape of the membrane 12 may be, for example, a circular shape, but may also be, for example, an elliptic shape or a quadrangular shape.

The driving element 13 is provided on the upper surface of the membrane 12. The shape of the driving element 13 may be designed to match the shape of the membrane 12. For example, when the planar shape of the membrane 12 is a circular shape, it is preferable to provide a circular driving element 13.

The membrane 12 can be vibrated by supplying a driving signal to the driving element 13 from a driving unit 20. The vibration of the membrane 12 can cause a liquid droplet 310 containing the fluorescent-stained cells 350 to be discharged through the nozzle 111.

When a piezoelectric element is used as the driving element 13, for example, the driving element 13 may have a structure obtained by providing the upper surface and the lower surface of the piezoelectric material with electrodes across which a voltage is to be applied. In this case, when the driving unit 20 applies a voltage across the upper and lower electrodes of the piezoelectric element, a compressive stress is applied in the horizontal direction of the drawing sheet, making it possible for the membrane 12 to vibrate in the upward-downward direction of the drawing sheet. As the piezoelectric material, for example, lead zirconate titanate (PZT) may be used. In addition, various piezoelectric materials can be used, such as bismuth iron oxide, metal niobate, barium titanate, or materials obtained by adding metals or different oxides to these materials.

The light source 30 is configured to irradiate a flying liquid droplet 310 with light L. A flying state means a state from when the liquid droplet 310 is discharged from a liquid droplet discharging unit 10 until when the liquid droplet 310 lands on the landing target. A flying liquid droplet 310 has an approximately spherical shape at the position at which the liquid droplet 310 is irradiated with the light L. The beam shape of the light L is an approximately circular shape.

It is preferable that the beam diameter of the light L be from about 10 times through 100 times as great as the diameter of the liquid droplet 310. This is for ensuring that the liquid droplet 310 is irradiated with the light L from the light source 30 without fail even when the position of the liquid droplet 310 fluctuates.

However, it is not preferable if the beam diameter of the light L is much greater than 100 times as great as the diameter of the liquid droplet 310. This is because the energy density of the light with which the liquid droplet 310 is irradiated is reduced, to lower the light volume of fluorescence Lf to be emitted upon the light L serving as excitation light, making it difficult for the light receiving element 60 to detect the fluorescence Lf.

It is preferable that the light L emitted by the light source 30 be pulse light. It is preferable to use, for example, a solid-state laser, a semiconductor laser, and a dye laser. When the light L is pulse light, the pulse width is preferably 10 microseconds or less and more preferably 1 microsecond or less. The energy per unit pulse is preferably roughly 0.1 microjoules or higher and more preferably 1 microjoule or higher, although significantly depending on the optical system such as presence or absence of light condensation.

The light receiving element 60 is configured to receive fluorescence Lf emitted by the fluorescent-stained cell 350 upon absorption of the light L as excitation light, when the fluorescent-stained cell 350 is contained in a flying liquid droplet 310. Because the fluorescence Lf is emitted to all directions from the fluorescent-stained cell 350, the light receiving element 60 can be disposed at an arbitrary position at which the fluorescence Lf is receivable. Here, in order to improve contrast, it is preferable to dispose the light receiving element 60 at a position at which direct incidence of the light L emitted by the light source 30 to the light receiving element 60 does not occur.

The light receiving element 60 is not particularly limited and may be appropriately selected depending on the intended purpose so long as the light receiving element 60 is an element capable of receiving the fluorescence Lf emitted by the fluorescent-stained cell 350. An optical sensor configured to receive fluorescence from a cell in a liquid droplet when the liquid droplet is irradiated with light having a specific wavelength is preferable. Examples of the light receiving element 60 include one-dimensional elements such as a photodiode and a photosensor. When high-sensitivity measurement is needed, it is preferable to use a photomultiplier tube and an Avalanche photodiode. As the light receiving element 60, two-dimensional elements such as a CCD (Charge Coupled Device), a CMOS (Complementary Metal Oxide Semiconductor), and a gate CCD may be used.

The fluorescence Lf emitted by the fluorescent-stained cell 350 is weaker than the light L emitted by the light source 30. Therefore, a filter configured to attenuate the wavelength range of the light L may be installed at a preceding stage (light receiving surface side) of the light receiving element 60. This enables the light receiving element 60 to obtain an extremely highly contrastive image of the fluorescent-stained cell 350. As the filter, for example, a notch filter configured to attenuate a specific wavelength range including the wavelength of the light L may be used.

As described above, it is preferable that the light L emitted by the light source 30 be pulse light. The light L emitted by the light source 30 may be continuously oscillating light. In this case, it is preferable to control the light receiving element 60 to be capable of receiving light at a timing at which a flying liquid droplet 310 is irradiated with the continuously oscillating light, to make the light receiving element 60 receive the fluorescence Lf.

Figure 8:
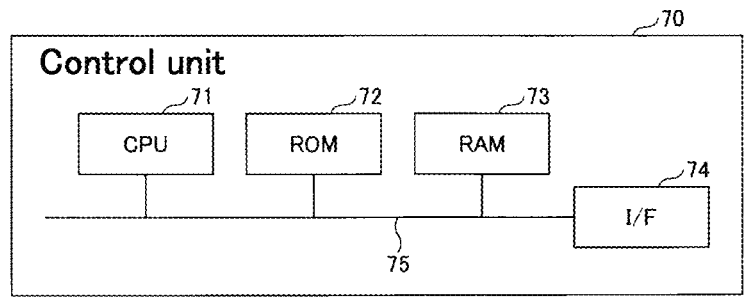
FIG. 8 is a diagram illustrating hardware blocks of a control unit of FIG. 7.
Figure 9:
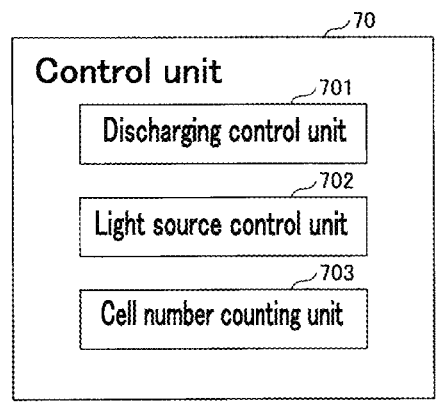
FIG. 9 is a diagram illustrating functional blocks of a control unit of FIG. 7.
Figure 10:
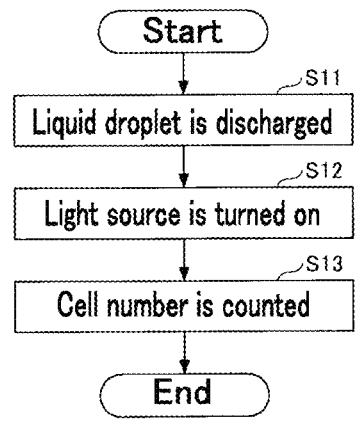
FIG. 10 is a flowchart illustrating an example of an operation of a liquid droplet forming device.

The control unit 70 has a function of controlling the driving unit 20 and the light source 30. The control unit 70 also has a function of obtaining information that is based on the light volume received by the light receiving element 60 and counting the number of fluorescent-stained cells 350 contained in the liquid droplet 310 (the case where the number is zero is also included). With reference to FIG. 8 to FIG. 10, an operation of the liquid droplet forming device 1 including an operation of the control unit 70 will be described below.

FIG. 8 is a diagram illustrating hardware blocks of the control unit of FIG. 7. FIG. 9 is a diagram illustrating functional blocks of the control unit of FIG. 7. FIG. 10 is a flowchart illustrating an example of the operation of the liquid droplet forming device.

As illustrated in FIG. 8, the control unit 70 includes a CPU 71, a ROM 72, a RAM 73, an I/F 74, and a bus line 75. The CPU 71, the ROM 72, the RAM 73, and the I/F 74 are coupled to one another via the bus line 75.

The CPU 71 is configured to control various functions of the control unit 70. The ROM 72 serving as a memory unit is configured to store programs to be executed by the CPU 71 for controlling the various functions of the control unit 70 and various information. The RAM 73 serving as a memory unit is configured to be used as, for example, the work area of the CPU 71. The RAM 73 is also configured to be capable of storing predetermined information for a temporary period of time. The I/F 74 is an interface configured to couple the liquid droplet forming device 1 to, for example, another device. The liquid droplet forming device 1 may be coupled to, for example, an external network via the I/F 74.

As illustrated in FIG. 9, the control unit 70 includes a discharging control unit 701, a light source control unit 702, and a cell number counting unit (cell number sensing unit) 703 as functional blocks.

With reference to FIG. 9 and FIG. 10, particle number counting by the liquid droplet forming device 1 will be described. In the step S11, the discharging control unit 701 of the control unit 70 outputs an instruction for discharging to the driving unit 20. Upon reception of the instruction for discharging from the discharging control unit 701, the driving unit 20 supplies a driving signal to the driving element 13 to vibrate the membrane 12. The vibration of the membrane 12 causes a liquid droplet 310 containing a fluorescent-stained cell 350 to be discharged through the nozzle 111.

Next, in the step S12, the light source control unit 702 of the control unit 70 outputs an instruction for lighting to the light source 30 in synchronization with the discharging of the liquid droplet 310 (in synchronization with a driving signal supplied by the driving unit 20 to the liquid droplet discharging unit 10). In accordance with this instruction, the light source 30 is turned on to irradiate the flying liquid droplet 310 with the light L.

Here, the light is emitted by the light source 30, not in synchronization with discharging of the liquid droplet 310 by the liquid droplet discharging unit 10 (supplying of the driving signal to the liquid droplet discharging unit 10 by the driving unit 20), but in synchronization with the timing at which the liquid droplet 310 has come flying to a predetermined position in order for the liquid droplet 310 to be irradiated with the light L. That is, the light source control unit 702 controls the light source 30 to emit light at a predetermined period of time of delay from the discharging of the liquid droplet 310 by the liquid droplet discharging unit 10 (from the driving signal supplied by the driving unit 20 to the liquid droplet discharging unit 10).

For example, the speed v of the liquid droplet 310 to be discharged when the driving signal is supplied to the liquid droplet discharging unit 10 may be measured beforehand. Based on the measured speed v, the time t taken from when the liquid droplet 310 is discharged until when the liquid droplet 310 reaches the predetermined position may be calculated, in order that the timing of light irradiation by the light source 30 may be delayed from the timing at which the driving signal is supplied to the liquid droplet discharging unit 10 by the period of time oft. This enables a good control on light emission, and can ensure that the liquid droplet 310 is irradiated with the light from the light source 30 without fail.

Next, in the step S13, the cell number counting unit 703 of the control unit 70 counts the number of fluorescent-stained cells 350 contained in the liquid droplet 310 (the case where the number is zero is also included) based on information from the light receiving element 60. The information from the light receiving element 60 indicates the luminance (light volume) and the area value of the fluorescent-stained cell 350.

The cell number counting unit 703 can count the number of fluorescent-stained cells 350 by, for example, comparing the light volume received by the light receiving element 60 with a predetermined threshold. In this case, a one-dimensional element may be used or a two-dimensional element may be used as the light receiving element 60.

When a two-dimensional element is used as the light receiving element 60, the cell number counting unit 703 may use a method of performing image processing for calculating the luminance or the area of the fluorescent-stained cell 350 based on a two-dimensional image obtained from the light receiving element 60. In this case, the cell number counting unit 703 can count the number of fluorescent-stained cells 350 by calculating the luminance or the area value of the fluorescent-stained cell 350 by image processing and comparing the calculated luminance or area value with a predetermined threshold.

The fluorescent-stained cell 350 may be a cell or a stained cell. A stained cell means a cell stained with a fluorescent pigment or a cell that can express a fluorescent protein.

The fluorescent pigment for the stained cell is not particularly limited and may be appropriately selected depending on the intended purpose. Examples of the fluorescent pigment include fluoresceins, rhodamines, coumarins, pyrenes, cyanines, and azo pigments. One of these fluorescent pigments may be used alone or two or more of these fluorescent pigments may be used in combination. Among these fluorescent pigments, eosin, Evans blue, trypan blue, rhodamine 6G, rhodamine B, and Rhodamine 123 are more preferable. Examples of the fluorescent protein include Sirius, EBFP, ECFP, mTurquoise, TagCFP, AmCyan, mTFP1, MidoriishiCyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. One of these fluorescent proteins may be used alone or two or more of these fluorescent proteins may be used in combination.

In this way, in the liquid droplet forming device 1, the driving unit 20 supplies a driving signal to the liquid droplet discharging unit 10 retaining the cell suspension 300 suspending fluorescent-stained cells 350 to cause the liquid droplet discharging unit 10 to discharge a liquid droplet 310 containing the fluorescent-stained cell 350, and the flying liquid droplet 310 is irradiated with the light L from the light source 30. Then, the fluorescent-stained cell 350 contained in the flying liquid droplet 310 emits the fluorescence Lf upon the light L serving as excitation light, and the light receiving element 60 receives the fluorescence Lf. Then, the cell number counting unit 703 counts the number of fluorescent-stained cells 350 contained in the flying liquid droplet 310, based on information from the light receiving element 60.

That is, the liquid droplet forming device 1 is configured for on-the-spot actual observation of the number of fluorescent-stained cells 350 contained in the flying liquid droplet 310. This can realize a better accuracy than hitherto obtained, in counting the number of fluorescent-stained cells 350. Moreover, because the fluorescent-stained cell 350 contained in the flying liquid droplet 310 is irradiated with the light L and emits the fluorescence Lf that is to be received by the light receiving element 60, an image of the fluorescent-stained cell 350 can be obtained with a high contrast, and the frequency of occurrence of erroneous counting of the number of fluorescent-stained cells 350 can be reduced.

FIG. 11 is an exemplary diagram illustrating a modified example of the liquid droplet forming device of FIG. 7. As illustrated in FIG. 11, a liquid droplet forming device 1A is different from the liquid droplet forming device 1 (see FIG. 7) in that a mirror 40 is arranged at the preceding stage of the light receiving element 60. Description about components that are the same as in the embodiment already described may be skipped.

In the liquid droplet forming device 1A, arranging the mirror 40 at the perceiving stage of the light receiving element 60 can improve the degree of latitude in the layout of the light receiving element 60.

For example, in the layout of FIG. 7, when a nozzle 111 and a landing target are brought close to each other, there is a risk of occurrence of interference between the landing target (although not illustrated in FIG. 7, corresponding to, for example, the cell contained base 700 of FIG. 6) and the optical system (particularly, the light receiving element 60) of the liquid droplet forming device 1. With the layout of FIG. 11, occurrence of interference can be avoided.

That is, by installing the light receiving element 60 in a region present in a direction opposite to a direction in which a liquid droplet is discharged from a discharging surface of the liquid droplet discharging unit as illustrated in FIG. 11, it is possible to reduce the distance (gap) between the landing target on which a liquid droplet 310 is landed and the nozzle 111 and suppress landing on a wrong position. As a result, the dispensing accuracy can be improved.

FIG. 12 is an exemplary diagram illustrating another modified example of the liquid droplet forming device of FIG. 7. As illustrated in FIG. 12, a liquid droplet forming device 1B is different from the liquid droplet forming device 1 (see FIG. 7) in that a light receiving element 61 configured to receive fluorescence $Lf_2$ emitted by the fluorescent-stained cell 350 is provided in addition to the light receiving element 60 configured to receive fluorescence $Lf_1$ emitted by the fluorescent-stained cell 350. Description about components that are the same as in the embodiment already described may be skipped.

The fluorescences $Lf_1$ and $Lf_2$ represent parts of fluorescence emitted to all directions from the fluorescent-stained cell 350. The light receiving elements 60 and 61 can be disposed at arbitrary positions at which the fluorescence emitted to different directions by the fluorescent-stained cell 350 is receivable. Three or more light receiving elements may be disposed at positions at which the fluorescence emitted to different directions by the fluorescent-stained cell 350 is receivable. The light receiving elements may have the same specifications or different specifications.

With 1 light receiving element, when a plurality of fluorescent-stained cells 350 are contained in a flying liquid droplet 310, there is a risk that the cell number counting unit 703 may erroneously count the number of fluorescent-stained cells 350 contained in the liquid droplet 310 (a risk that a counting error may occur) because the fluorescent-stained cells 350 may overlap each other.

Figure 13A:
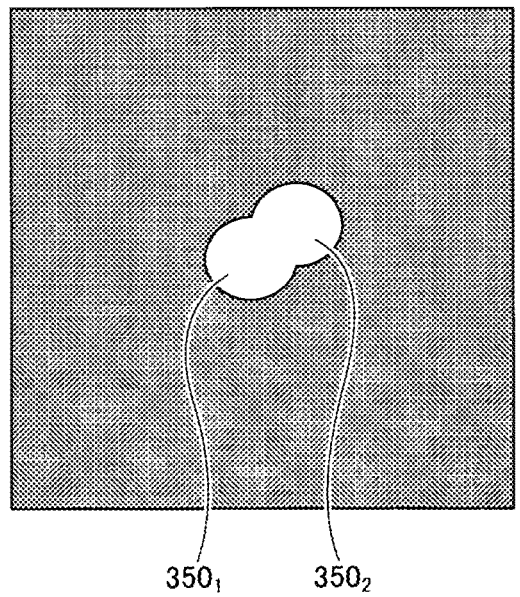
FIG. 13A is a diagram illustrating a case where 2 fluorescent particles are contained in a flying liquid droplet.
Figure 13B:
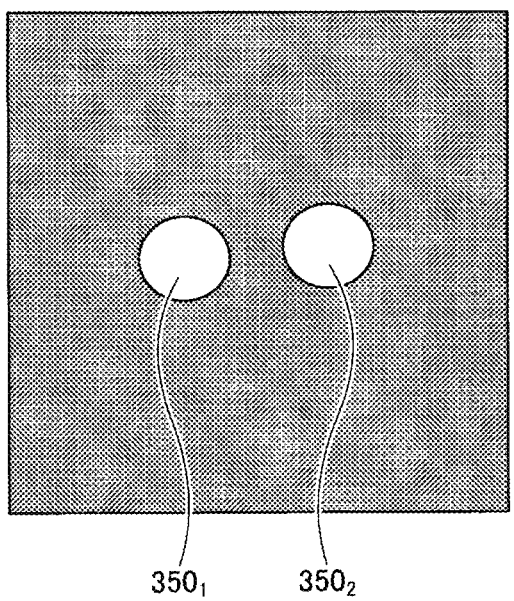
FIG. 13B is a diagram illustrating a case where 2 fluorescent particles are contained in a flying liquid droplet.

FIG. 13A and FIG. 13B are diagrams illustrating a case where 2 fluorescent-stained cells are contained in a flying liquid droplet. For example, as illustrated in FIG. 13A, there may be a case where fluorescent-stained cells $350_1$ and $350_2$ overlap each other, or as illustrated in FIG. 13B, there may be a case where the fluorescent-stained cells $350_1$ and $350_2$ do not overlap each other. By providing two or more light receiving elements, it is possible to reduce the influence of overlap of the fluorescent-stained cells.

As described above, the cell number counting unit 703 can count the number of fluorescent particles, by calculating the luminance or the area value of fluorescent particles by image processing and comparing the calculated luminance or area value with a predetermined threshold.

When two or more light receiving elements are installed, it is possible to suppress occurrence of a counting error, by adopting the data indicating the maximum value among the luminosities or area values obtained from these light receiving elements. This will be described in more detail with reference to FIG. 14.

Figure 14:
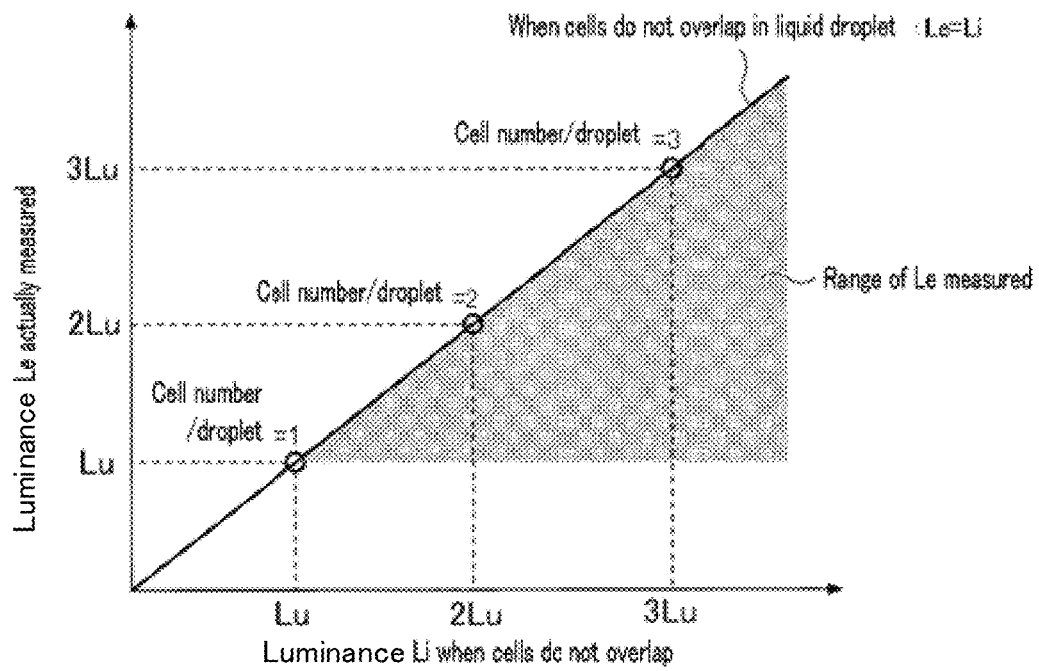
FIG. 14 is a graph plotting an example of a relationship between a luminance Li when particles do not overlap each other and a luminance Le actually measured.

FIG. 14 is a graph plotting an example of a relationship between a luminance Li when particles do not overlap each other and a luminance Le actually measured. As plotted in FIG. 14, when particles in the liquid droplet do not overlap each other, Le is equal to Li. For example, in the case where the luminance of 1 cell is assumed to be Lu, Le is equal to Lu when the number of cells per droplet is 1, and Le is equal to nLu when the number of particles per droplet is n (n: natural number).

However, actually, when n is 2 or greater, because particles may overlap each other, the luminance to be actually measured is Lu≤Le≤nLu (the half-tone dot meshed portion in FIG. 14). Hence, when the number of cells per droplet is n, the threshold may be set to, for example, (nLu−Lu/2) ≤threshold<(nLu+Lu/2). When a plurality of light receiving elements are installed, it is possible to suppress occurrence of a counting error, by adopting the maximum value among the data obtained from these light receiving elements. An area value may be used instead of luminance.

When a plurality of light receiving elements are installed, the number of particles may be determined according to an algorithm for estimating the number of cells based on a plurality of shape data to be obtained.

As can be understood, with the plurality of light receiving elements configured to receive fluorescence emitted to different directions by the fluorescent-stained cell 350, the liquid droplet forming device 1B can further reduce the frequency of occurrence of erroneous counting of the number of fluorescent-stained cells 350.

Figure 15:
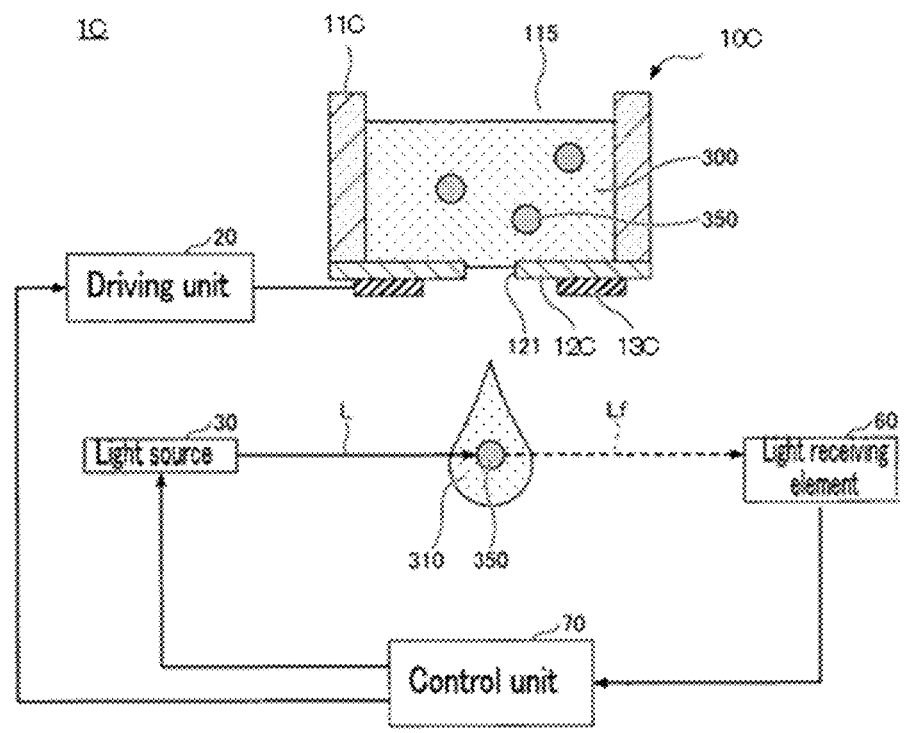
FIG. 15 is an exemplary diagram illustrating another modified example of a liquid droplet forming device of FIG. 7.

FIG. 15 is an exemplary diagram illustrating another modified example of the liquid droplet forming device of FIG. 7. As illustrated in FIG. 15, a liquid droplet forming device 1C is different from the liquid droplet forming device 1 (see FIG. 7) in that a liquid droplet discharging unit 10C is provided instead of the liquid droplet discharging unit 10. Description about components that are the same as in the embodiment already described may be skipped.

The liquid droplet discharging unit 10C includes a liquid chamber 11C, a membrane 12C, and a driving element 13C. At the top, the liquid chamber 11C has an atmospherically exposed portion 115 configured to expose the interior of the liquid chamber 11C to the atmosphere, and air bubbles mixed in the cell suspension 300 can be evacuated through the atmospherically exposed portion 115.

The membrane 12C is a film-shaped member secured at the lower end of the liquid chamber 11C. A nozzle 121, which is a through-hole, is formed in approximately the center of the membrane 12C, and the vibration of the membrane 12C causes the cell suspension 300 retained in the liquid chamber 11C to be discharged through the nozzle 121 in the form of a liquid droplet 310. Because the liquid droplet 310 is formed by the inertia of the vibration of the membrane 12C, it is possible to discharge the cell suspension 300 even when the cell suspension 300 has a high surface tension (a high viscosity). The planer shape of the membrane 12C may be, for example, a circular shape, but may also be, for example, an elliptic shape or a quadrangular shape.

The material of the membrane 12C is not particularly limited. However, if the material of the membrane 12C is extremely flexible, the membrane 12C easily undergo vibration and is not easily able to stop vibration immediately when there is no need for discharging. Therefore, a material having a certain degree of hardness is preferable. As the material of the membrane 12C, for example, a metal material, a ceramic material, and a polymeric material having a certain degree of hardness can be used.

Particularly, when a cell is used as the fluorescent-stained cell 350, the material of the membrane is preferably a material having a low adhesiveness with the cell or proteins. Generally, adhesiveness of cells is said to be dependent on the contact angle of the material with respect to water. When the material has a high hydrophilicity or a high hydrophobicity, the material has a low adhesiveness with cells. As the material having a high hydrophilicity, various metal materials and ceramics (metal oxides) can be used. As the material having a high hydrophobicity, for example, fluororesins can be used.

Other examples of such materials include stainless steel, nickel, and aluminum, and silicon dioxide, alumina, and zirconia. In addition, it is conceivable to reduce cell adhesiveness by coating the surface of the material. For example, it is possible to coat the surface of the material with the metal or metal oxide materials described above, or coat the surface of the material with a synthetic phospholipid polymer mimicking a cellular membrane (e.g., LIPIDURE available from NOF Corporation).

It is preferable that the nozzle 121 be formed as a through-hole having a substantially perfect circle shape in approximately the center of the membrane 12C. In this case, the diameter of the nozzle 121 is not particularly limited but is preferably twice or more greater than the size of the fluorescent-stained cell 350 in order to prevent the nozzle 121 from being clogged with the fluorescent-stained cell 350. When the fluorescent-stained cell 350 is, for example, an animal cell, particularly, a human cell, the diameter of the nozzle 121 is preferably 10 micrometers or greater and more preferably 100 micrometers or greater in conformity with the cell used, because a human cell typically has a size of about from 5 micrometers through 50 micrometers.

On the other hand, when a liquid droplet is extremely large, it is difficult to achieve an object of forming a minute liquid droplet. Therefore, the diameter of the nozzle 121 is preferably 200 micrometers or less. That is, in the liquid droplet discharging unit 10C, the diameter of the nozzle 121 is typically in the range of from 10 micrometers through 200 micrometers.

The driving element 13C is formed on the lower surface of the membrane 12C. The shape of the driving element 13C can be designed to match the shape of the membrane 12C. For example, when the planar shape of the membrane 12C is a circular shape, it is preferable to form a driving element 13C having an annular (ring-like) planar shape around the nozzle 121. The driving method for driving the driving element 13C may be the same as the driving method for driving the driving element 13.

The driving unit 20 can selectively (for example, alternately) apply to the driving element 13C, a discharging waveform for vibrating the membrane 12C to form a liquid droplet 310 and a stirring waveform for vibrating the membrane 12C to an extent until which a liquid droplet 310 is not formed.

For example, the discharging waveform and the stirring waveform may both be rectangular waves, and the driving voltage for the stirring waveform may be set lower than the driving voltage for the discharging waveform. This makes it possible for a liquid droplet 310 not to be formed by application of the stirring waveform. That is, it is possible to control the vibration state (degree of vibration) of the membrane 12C depending on whether the driving voltage is high or low.

In the liquid droplet discharging unit 10C, the driving element 13C is formed on the lower surface of the membrane 12C. Therefore, when the membrane 12 is vibrated by means of the driving element 13C, a flow can be generated in a direction from the lower portion to the upper portion in the liquid chamber 11C.

Here, the fluorescent-stained cells 350 move upward from lower positions, to generate a convection current in the liquid chamber 11C to stir the cell suspension 300 containing the fluorescent-stained cells 350. The flow from the lower portion to the upper portion in the liquid chamber 11C disperses the settled, aggregated fluorescent-stained cells 350 uniformly in the liquid chamber 11C.

That is, by applying the discharging waveform to the driving element 13C and controlling the vibration state of the membrane 12C, the driving unit 20 can cause the cell suspension 300 retained in the liquid chamber 11C to be discharged through the nozzle 121 in the form of a liquid droplet 310. Further, by applying the stirring waveform to the driving element 13C and controlling the vibration state of the membrane 12C, the driving unit 20 can stir the cell suspension 300 retained in the liquid chamber 11C. During stirring, no liquid droplet 310 is discharged through the nozzle 121.

In this way, stirring the cell suspension 300 while no liquid droplet 310 is being formed can prevent settlement and aggregation of the fluorescent-stained cells 350 over the membrane 12C and can disperse the fluorescent-stained cells 350 in the cell suspension 300 without unevenness. This can suppress clogging of the nozzle 121 and variation in the number of fluorescent-stained cells 350 in the liquid droplets 310 to be discharged. This makes it possible to stably discharge the cell suspension 300 containing the fluorescent-stained cells 350 in the form of liquid droplets 310 continuously for a long time.

In the liquid droplet forming device 1C, air bubbles may mix in the cell suspension 300 in the liquid chamber 11C. Also in this case, the liquid droplet forming device 1C can emit the air bubbles mixed in the cell suspension 300 to the outside air through the atmospherically exposed portion 115 provided at the top of the liquid chamber 11C. This enables continuous, stable formation of liquid droplets 310 without a need for disposing of a large amount of the liquid for air bubble elimination.

That is, the discharging state is affected when mixed air bubbles are present at a position near the nozzle 121 or when many mixed air bubbles are present over the membrane 12C. Therefore, in order to perform stable formation of liquid droplets for a long time, there is a need for eliminating the mixed air bubbles. Typically, mixed air bubbles present over the membrane 12C move upward autonomously or by vibration of the membrane 12C. Because the liquid chamber 11C is provided with the atmospherically exposed portion 115, the mixed air bubbles can be evacuated through the atmospherically exposed portion 115. This makes it possible to prevent occurrence of empty discharging even when air bubbles mix in the liquid chamber 11, enabling continuous, stable formation of liquid droplets 310.

At a timing at which a liquid droplet is not being formed, the membrane 12C may be vibrated to an extent until which a liquid droplet is not formed, in order to positively move the air bubbles upward in the liquid chamber 11C.

—Electric or Magnetic Detection Method—

Figure 16:
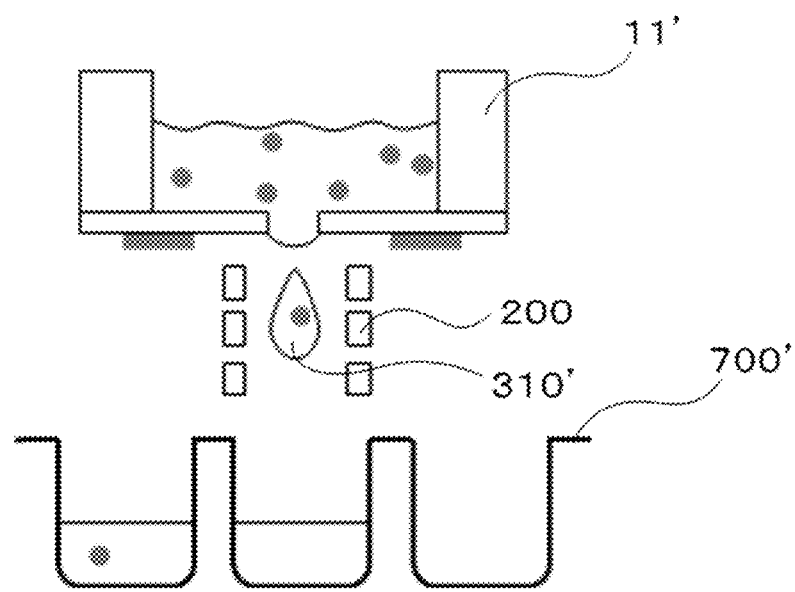
FIG. 16 is an exemplary diagram illustrating another example of a liquid droplet forming device.

In the case of the electric or magnetic detection method, as illustrated in FIG. 16, a coil 200 configured to count the number of cells is installed as a sensor immediately below a discharging head configured to discharge the cell suspension onto a cell contained base 700' from a liquid chamber 11' in the form of a liquid droplet 310'. Cells are modified with a specific protein and coated with magnetic beads that can adhere to the cells. Therefore, when the cells to which magnetic beads adhere pass through the coil, an induced current is generated to enable detection of presence or absence of the cells in the flying liquid droplet. Generally, cells have proteins specific to the cells on the surfaces of the cells. Modification of magnetic beads with antibodies that can adhere to the proteins enables adhesion of the magnetic beads to the cells. As such magnetic beads, a ready-made product can be used. For example, DYNABEADS (registered trademark) available from Veritas Corporation can be used.

The position of the sensor is not particularly limited and may be appropriately selected depending on the intended purpose. Examples of the position of the sensor include: a region between the liquid droplet discharging unit and the cell contained base; and a region other than the region between the cell contained base and the liquid droplet discharging unit, particularly a region present in a direction opposite to a direction in which a liquid droplet is discharged from a discharging surface of the liquid droplet discharging unit.

The region present in a direction opposite to a direction in which a liquid droplet is discharged from a discharging surface of the liquid droplet discharging unit means a space present at the liquid droplet discharging unit side of the surface from which a liquid droplet is discharged.

<<Operation for Observing Cells Before Discharging>>

Figure 17:
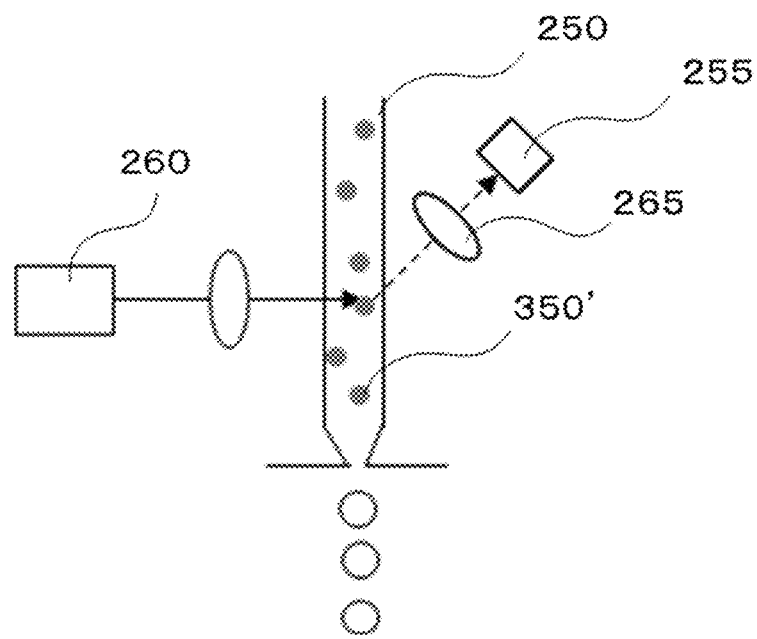
FIG. 17 is an exemplary diagram illustrating an example of a method for counting cells that have passed through a micro-flow path.
Figure 18:
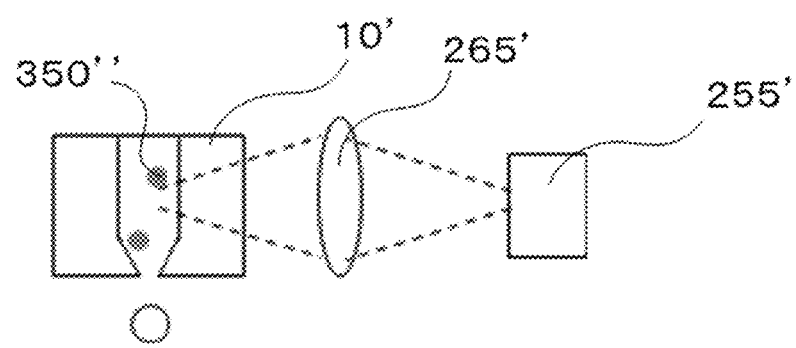
FIG. 18 is an exemplary diagram illustrating an example of a method for capturing an image of a portion near a nozzle portion of a discharging head.

The operation for observing cells before discharging may be performed by, for example, a method for counting cells 350' that have passed through a micro-flow path 250 illustrated in FIG. 17 or a method for capturing an image of a portion near a nozzle portion of a discharging head illustrated in FIG. 18. The method of FIG. 17 is a method used in a cell sorter device, and, for example, CELL SORTER SH800 available from Sony Corporation can be used. In FIG. 17, a light source 260 emits laser light into the micro-flow path 250, and a detector 255 detects scattered light or fluorescence through a condenser lens 265. This enables discrimination of presence or absence of cells or the kind of the cells, while a liquid droplet is being formed. Based on the number of cells that have passed through the micro-flow path 250, this method enables estimation of the number of cells that have landed in a predetermined cell contained region. As the discharging head 10' illustrated in FIG. 18, a single cell printer available from Cytena GmbH can be used. In FIG. 18, it is possible to estimate the number of cells that have landed in a predetermined cell contained region, by capturing an image of the portion near the nozzle portion with an image capturing unit 255' through a lens 265' before discharging and estimating based on the captured image that cells 350" present near the nozzle portion have been discharged, or by estimating the number of cells that are considered to have been discharged based on a difference between images captured before and after discharging. The method of FIG. 18 is more preferable because the method enables on-demand liquid droplet formation, whereas the method of FIG. 17 for counting cells that have passed through the micro-flow path generates liquid droplets continuously.

<<Operation for Counting Cells After Landing>>

The operation for counting cells after landing may be performed by a method for detecting fluorescent-stained cells by observing the cell contained regions in the cell contained base with, for example, a fluorescence microscope. This method is described in, for example, Sangjun et al., PLoS One, Volume 6(3), e17455.

Methods for observing cells before discharging a liquid droplet or after landing have the problems described below. Depending on the kind of the cell contained base to be produced, it is the most preferable to observe cells in a liquid droplet that is being discharged. In the method for observing cells before discharging, the number of cells that are considered to have landed is counted based on the number of cells that have passed through a flow path and image observation before discharging (and after discharging). Therefore, it is not confirmed whether the cells have actually been discharged, and an unexpected error may occur. For example, there may be a case where because the nozzle portion is stained, a liquid droplet is not discharged appropriately but adheres to the nozzle plate, thus failing to make the cells in the liquid droplet land. Moreover, there may occur a problem that the cells stay behind in a narrow region of the nozzle portion, or a discharging operation causes the cells to move beyond assumption and go outside the range of observation. The method for detecting cells on the cell contained base after landing also have problems. First, there is a need for preparing a base that can be observed with a microscope. As a cell contained base that can be observed, it is common to use a base having a transparent, flat bottom surface, particularly a base having a bottom surface formed of glass. However, there is a problem that such a special cell contained base is incompatible with use of ordinary cell contained regions (for example, wells). Further, when the number of cells is large, such as some tens of cells, there is a problem that correct counting is impossible because the cells may overlap with each other. Accordingly, it is preferable to perform the operation for observing cells before discharging and the operation for counting cells after landing, in addition to counting the number of cells contained in a liquid droplet with a sensor and a particle number (cell number) counting unit after the liquid droplet is discharged and before the liquid droplet lands in a cell contained region.

As the light receiving element, a light receiving element including 1 or a small number of light receiving portion(s), such as a photodiode, an Avalanche photodiode, and a photomultiplier tube may be used. In addition, a two-dimensional sensor including light receiving elements in a two-dimensional array formation, such as a CCD (Charge Coupled Device), a CMOS (Complementary Metal Oxide Semiconductor), and a gate CCD may be used.

Figure 19:
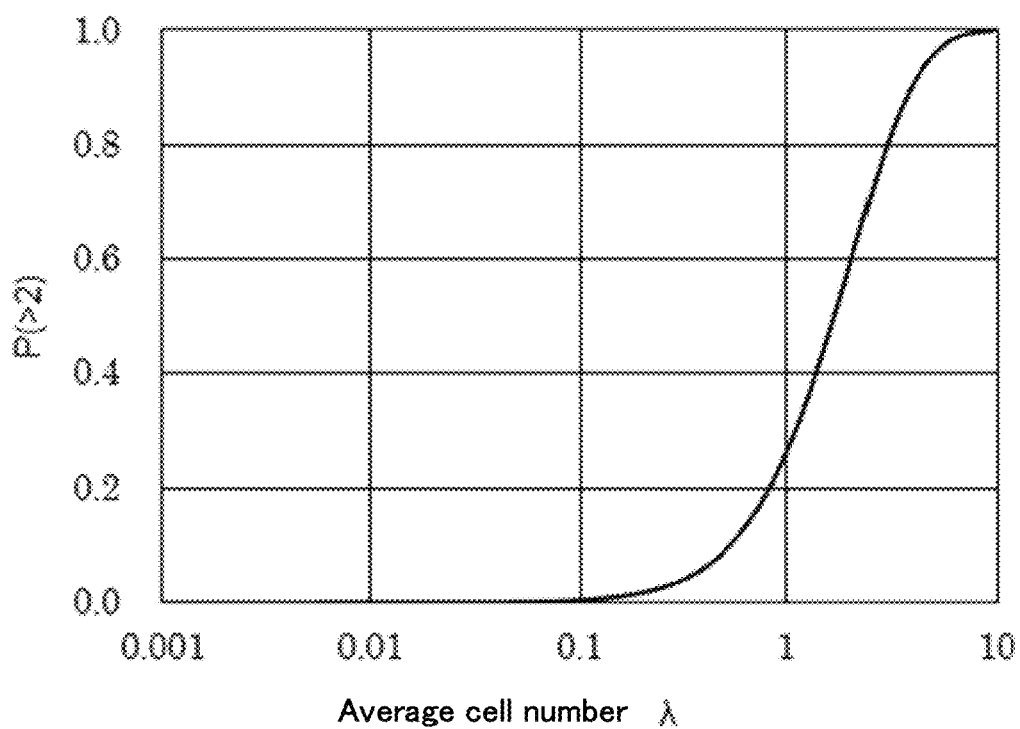
FIG. 19 is a graph plotting a relationship between a probability P (>2) and an average cell number.

When using a light receiving element including 1 or a small number of light receiving portion(s), it is conceivable to determine the number of cells contained, based on the fluorescence intensity, using a calibration curve prepared beforehand. Here, binary detection of whether cells are present or absent in a flying liquid droplet is common. When the cell suspension is discharged in a state that the cell concentration is so sufficiently low that almost only 1 or 0 cell(s) will be contained in a liquid droplet, sufficiently accurate counting is available by the binary detection. On the premise that cells are randomly distributed in the cell suspension, the cell number in a flying liquid droplet is considered to conform to Poisson distribution, and the probability $P(>2)$ at which two or more cells are contained in a liquid droplet is represented by a formula (1) below. FIG. 19 is a graph plotting a relationship between the probability $P(>2)$ and an average cell number. Here, $\lambda$ is a value representing an average cell number in a liquid droplet and obtained by multiplying the cell concentration in the cell suspension by the volume of a liquid droplet discharged.

$$P(>2)=1-(1+\lambda)\times e^{-\lambda} \qquad \text{formula (1)}$$

When performing cell number counting by binary detection, in order to ensure accuracy, it is preferable that the probability $P(>2)$ be a sufficiently low value, and that $\lambda$ satisfy: $\lambda<0.15$, at which the probability $P(>2)$ is 1% or lower. The light source is not particularly limited and may be appropriately selected depending on the intended purpose, so long as the light source can excite fluorescence from cells. It is possible to use, for example, an ordinary lamp such as a mercury lamp and a halogen lamp to which a filter is applied for emission of a specific wavelength, a LED (Light Emitting Diode), and a laser. However, particularly when forming a minute liquid droplet of 1 nL or less, there is a need for irradiating a small region with a high light intensity. Therefore, use of a laser is preferable. As a laser light source, various commonly known lasers such as a solid-state laser, a gas laser, and a semiconductor laser can be used. The excitation light source may be a light source that is configured to continuously irradiate a region through which a liquid droplet passes or may be a light source that is configured for pulsed irradiation in synchronization with discharging of a liquid droplet at a timing delayed by a predetermined period of time from the operation for discharging the liquid droplet.

<Liquid Droplet Landing Step>

The liquid droplet landing step is a step of landing the liquid droplet in the at least one cell contained region in a manner that a predetermined number of cells are located in the at least one cell contained region.

A predetermined number means an arbitrarily set number. Here, what is meant is that the number of cells to be located in each cell contained region is arbitrarily set.

As the predetermined number, the same number of cells may be located to all cell contained regions of the cell contained base, or a plurality of groups (each group may also be referred to as "level") of cells containing the same number of cells may be provided in each cell contained region.

Locating means providing a predetermined article at a predetermined position.

Landing means making liquid droplets reach the cell contained regions.

The method for landing a liquid droplet is not particularly limited and may be appropriately selected depending on the intended purpose. Examples of the method include a method of repeating locating liquid droplets in one cell contained region until the predetermined number set for the cell contained region is reached, and then landing liquid droplets into another cell contained region until the predetermined number set for that cell contained region is reached, and a method of sequentially locating liquid droplets in the cell contained regions until the predetermined numbers set for the respective cell contained regions are reached.

"Sequentially" means "in order".

Figure 6:
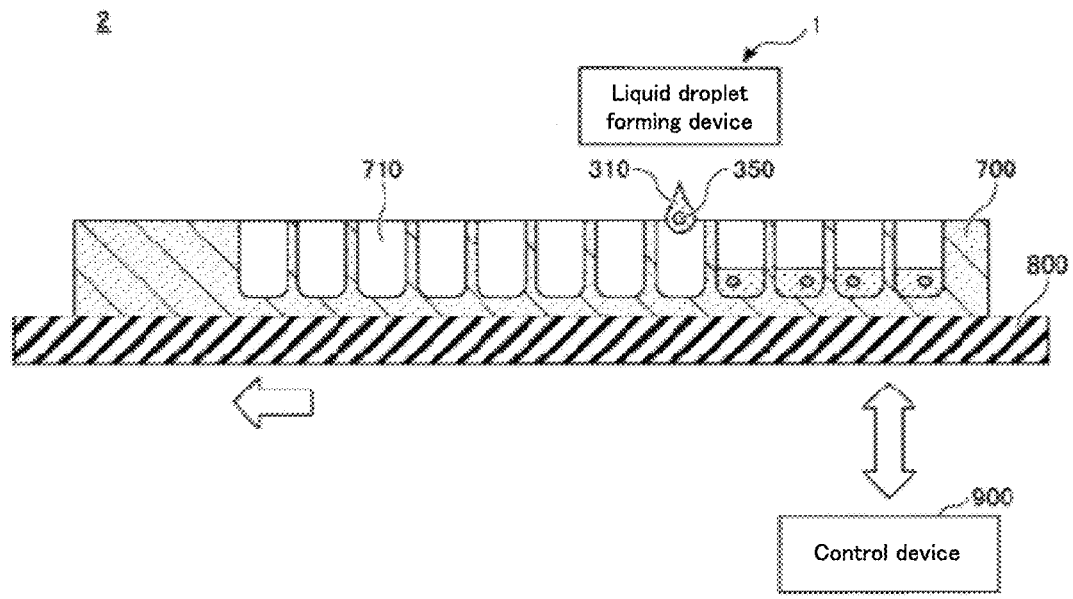
FIG. 6 is a schematic diagram illustrating an example of a device configured to land liquid droplets sequentially into cell contained regions of a cell contained base.

In FIG. 6, in the method for producing a cell contained base of the present disclosure, a cell contained base in which cell contained regions (concaves) are formed is secured on a movable stage, and by combination of driving of the stage with formation of liquid droplets from the discharging head, liquid droplets are sequentially landed in the cell contained regions (concaves). A method of moving the cell contained base along with moving the stage is described here. However, naturally, it is also possible to move the discharging head.

FIG. 6 is a schematic diagram illustrating an example of a device configured to land liquid droplets sequentially into cell contained regions of a cell contained base.

As illustrated in FIG. 6, a device (dispensing device) 2 configured to land liquid droplets includes a liquid droplet forming unit 1, a stage 800, and a control device 900.

A cell contained base 700 is disposed over a movable stage 800. The cell contained base 700 has a plurality of cell contained regions 710 (concaves) in which liquid droplets 310 discharged from a discharging head of the liquid droplet forming unit 1 land. The control device 900 is configured to move the stage 800 and control the relative positional relationship between the discharging head of the liquid droplet forming unit 1 and each cell contained region 710. This enables liquid droplets 310 containing fluorescent-stained cells 350 to be discharged sequentially into the cell contained regions 710 from the discharging head of the liquid droplet forming unit 1.

The control device 900 may be configured to include, for example, a CPU, a ROM, a RAM, and a main memory. In this case, various functions of the control device 900 can be realized by a program recorded in, for example, the ROM being read out into the main memory and executed by the CPU. However, a part or the whole of the control device 900 may be realized only by hardware. Alternatively, the control device 900 may be configured with, for example, physically a plurality of devices.

When landing the cell suspension into the cell contained regions, it is preferable to land the liquid droplets to be discharged into the cell contained regions, in a manner that a plurality of levels are obtained.

A plurality of levels mean a plurality of references serving as standards.

The plurality of levels mean a predetermined concentration gradient of the cell contained base, obtained by, for example, locating different plural numbers of cells including a nucleic acid having a specific base sequence in different cell contained regions. With a concentration gradient, the nucleic acid can be favorably used as a reagent for calibration curve. The plurality of levels can be controlled using values counted by the sensor.

<Step of Calculating Degrees of Certainty of Estimated Numbers of Nucleic Acids in Cell Suspension Producing Step, Liquid Droplet Landing Step, and Cell Number Counting Step>

The step of calculating degrees of certainty of estimated numbers of nucleic acids in the cell suspension producing step, the liquid droplet landing step, and the cell number counting step is a step of calculating the degree of certainty in each of the cell suspension producing step, the liquid droplet landing step, and the cell number counting step.

The degree of certainty of an estimated number of nucleic acids can be calculated in the same manner as calculating the degree of certainty in the cell suspension producing step.

The timing at which the degrees of certainty are calculated may be collectively in the next step to the cell number counting step as illustrated in FIG. 1, or may be at the end of each of the cell suspension producing step, the liquid droplet landing step, and the cell number counting step in order for the degrees of certainty to be summed in the next step to the cell number counting step. In other words, the degrees of certainty in these steps need only to be calculated at arbitrary timings by the time when summing is performed.

<Nucleic Acid Number Calculating Step>

The nucleic acid number calculating step is a step of calculating an average value for the number of nucleic acids contained in a cell contained region, based on at least any one of the cell cycles of the cells, the accuracy of the counted number of cells contained in the liquid droplet, and the ratio (accuracy) at which the liquid droplet lands within an intended range in the cell contained region.

The accuracy of the counted number of cells contained in the liquid droplet can be obtained by comparing the number of cells sensed by the sensor with a number of landed cells observed with a microscope.

By performing the nucleic acid number calculating step, it is possible to accurately recognize the number of nucleic acids having a specific base sequence contained in each cell contained region of the cell contained base produced.

<Outputting Step>

The outputting step is a step of outputting a counted value of the number of cells contained in the cell suspension that has landed in a cell contained region, counted by a particle number counting unit based on a detection result measured by a sensor.

The counted value means a total number of cells contained in the cell contained region, calculated by the particle number counting unit based on the detection result measured by the sensor.

The particle number counting unit is a unit configured to count up the number of cells measured by a sensor to calculate a total value.

Outputting means sending a value counted by a device such as a motor, communication equipment, and a calculator upon reception of an input to an external server serving as a count result memory unit in the form of electronic information, or printing the counted value as a printed matter.

In the outputting step, an observed value or an estimated value obtained by observing or estimating the number of cells or the number of nucleic acids in each cell contained region of a cell contained base during production of the cell contained base is output to an external memory unit.

Outputting may be performed at the same time as the cell number counting step, or may be performed after the cell number counting step.

<Recording Step>

The recording step is a step of recording the observed value or the estimated value output in the outputting step.

The recording step can be suitably performed by a recording unit.

Recording may be performed at the same time as the outputting step, or may be performed after the outputting step.

Recording means not only supplying information to a recording medium but also storing information in a memory unit.

<Nucleic Acid Extracting Step>

The nucleic acid extracting step is a step of extracting nucleic acids from cells in the cell contained region.

Extracting means destroying, for example, cellular membranes and cell walls to pick out nucleic acids.

As the method for extracting nucleic acids from cells, there is known a method of thermally treating cells at from 90 degrees C. through 100 degrees C. By a thermal treatment at 90 degrees C. or lower, there is a possibility that nucleic acids may not be extracted. By a thermal treatment at 100 degrees C. or higher, there is a possibility that nucleic acids may be decomposed. Here, it is preferable to perform thermal treatment with addition of a surfactant.

The surfactant is not particularly limited and may be appropriately selected depending on the intended purpose. Examples of the surfactant include ionic surfactants and nonionic surfactants. One of these surfactants may be used alone or two or more of these surfactants may be used in combination. Among these surfactants, nonionic surfactants are preferable because proteins are neither modified nor deactivated by nonionic surfactants, although depending on the addition amount of the nonionic surfactants.

Examples of the ionic surfactants include fatty acid sodium, fatty acid potassium, alpha-sulfo fatty acid ester sodium, sodium straight-chain alkyl benzene sulfonate, alkyl sulfuric acid ester sodium, alkyl ether sulfuric acid ester sodium, and sodium alpha-olefin sulfonate. One of these ionic surfactants may be used alone or two or more of these ionic surfactants may be used in combination. Among these ionic surfactants, fatty acid sodium is preferable and sodium dodecyl sulfate (SDS) is more preferable.

Examples of the nonionic surfactants include alkyl glycoside, alkyl polyoxyethylene ether (e.g., BRIJ series), octyl phenol ethoxylate (e.g., TRITON X series, IGEPAL CA series, NONIDET P series, and NIKKOL OP series), polysorbates (e.g., TWEEN series such as TWEEN 20), sorbitan fatty acid esters, polyoxyethylene fatty acid esters, alkyl maltoside, sucrose fatty acid esters, glycoside fatty acid esters, glycerin fatty acid esters, propylene glycol fatty acid esters, and fatty acid monoglyceride. One of these nonionic surfactants may be used alone or two or more of these nonionic surfactants may be used in combination. Among these nonionic surfactants, polysorbates are preferable.

The content of the surfactant is preferably 0.01% by mass or greater but 5.00% by mass or less relative to the total amount of the cell suspension in the cell contained region. When the content of the surfactant is 0.01% by mass or greater, the surfactant can be effective for DNA extraction. When the content of the surfactant is 5.00% by mass or less, inhibition against amplification can be prevented during PCR. As a numerical range in which both of these effects can be obtained, a range of 0.01% by mass or greater but 5.00% by mass or less is preferable.

The method described above may not be able to sufficiently extract a nucleic acid from a cell that has a cell wall. Examples of methods for such a case include an osmotic shock procedure, a freeze-thaw method, an enzymic digestive method, use of a nucleic acid extraction kit, an ultrasonic treatment method, a French press method, and a homogenizer method. Among these methods, an enzymic digestive method is preferable because the method can save loss of extracted nucleic acids.

<Other Steps>

Examples of the other steps include an enzyme deactivating step.

<<Enzyme Deactivating Step>>

The enzyme deactivating step is a step of deactivating an enzyme.

Examples of the enzyme include DNase, RNase, and an enzyme used in the nucleic acid extracting step in order to extract a nucleic acid.

The method for deactivating an enzyme is not particularly limited and may be appropriately selected depending on the intended purpose. A known method can be suitably used.

The cell contained base produced by the method for producing a cell contained base of the present disclosure is widely used in, for example, biotechnology-related industries, life science industries, and health care industries, and can be used suitably for, for example, applications such as equipment calibration or generation of calibration curves for infectious diseases.

In the case of working the plate as a reference plate for infectious diseases, the plate is applicable to methods stipulated as official analytical methods or officially announced methods.

Figure 20A:
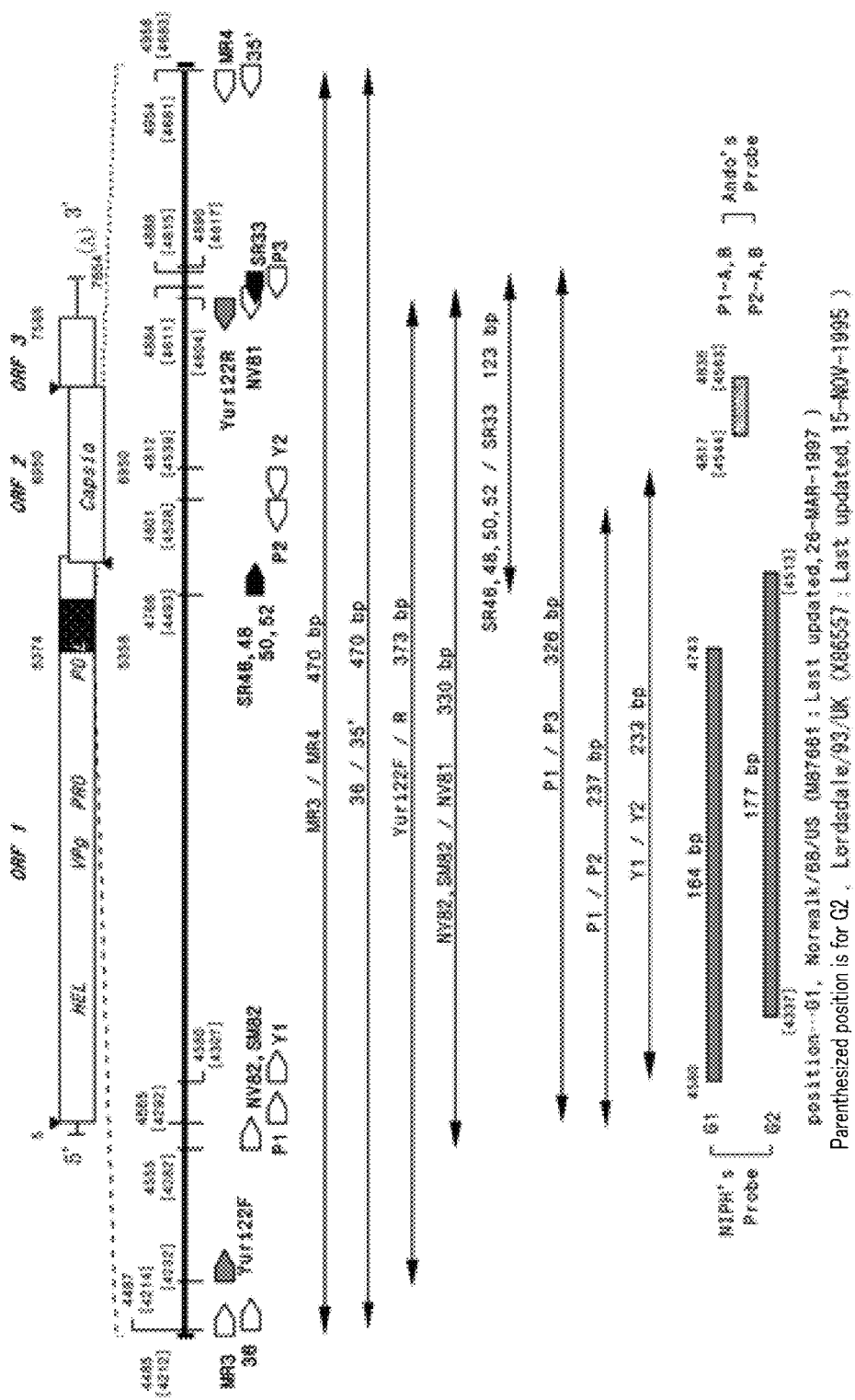
FIG. 20A is a diagram illustrating the positions of a primer and a probe in a portion of norovirus corresponding to an open reading frame 1.
Figure 20B:
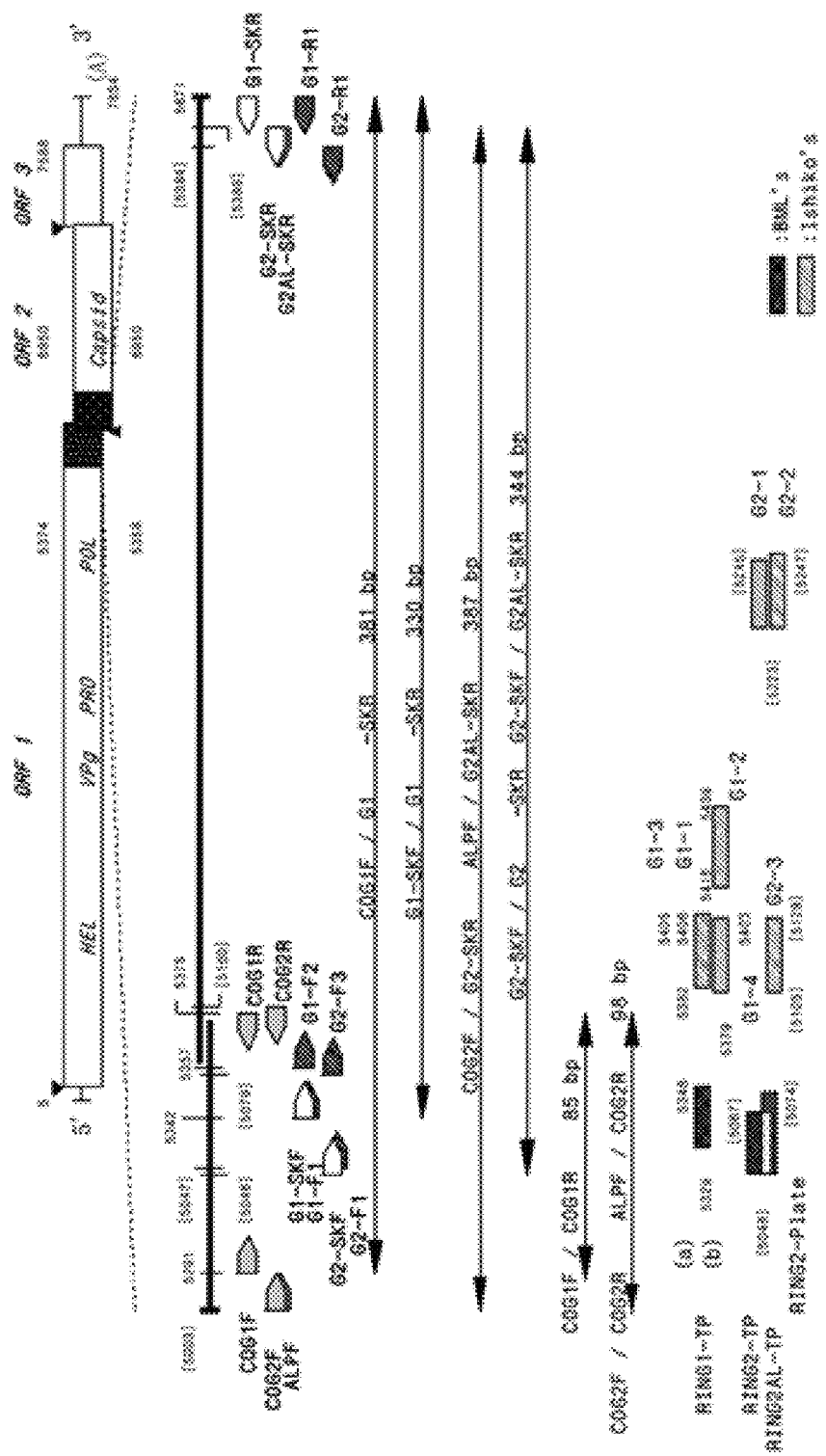
FIG. 20B is a diagram illustrating the positions of a primer and a probe in a portion of norovirus corresponding to an open reading frame 2.

Examples of official analytical methods include an official analytical method for norovirus (No. 0514004 issued by monitoring manager of food safety department). FIG. 20A is a diagram illustrating the positions of a primer and a probe in a portion of norovirus corresponding to an open reading frame 1. FIG. 20B is a diagram illustrating the positions of a primer and a probe in a portion of norovirus corresponding to an open reading frame 2.

In the official analytical method for norovirus, for example, the nucleic acid sequences in the regions illustrated in FIG. 20A and FIG. 20B are introduced into cells by a transgenesis technique. A known number (from 10 through $10^7$) of cells including these nucleic acid sequences specific to norovirus are dispensed into cell contained regions. Here, in a low copy number range (from 10 through $10^3$), the dilution method has a low accuracy, and values on a calibration curve may not be constant, leading to a risk that accuracy of a detected copy number may be poor. Hence, use of ink jetting or a cell sorter having a high dispensing accuracy is suitable for dispensing, because a higher accuracy will be obtained. Next, a sample extracted by a method specified in No. 0514004 issued by monitoring manager of food safety department is dispensed into empty cell contained regions and allowed to undergo a reaction by real-time PCR with addition of a primer, an enzyme, a TaqMan probe, and water. In this way, it is possible to confirm presence or absence of norovirus. In the case of RT-PCR, it is possible to confirm presence or absence of norovirus by adding the materials described above except the TaqMan probe, allowing the materials to undergo a reaction with a thermal cycler, and subjecting the obtained sample to electrophoresis.

(Method for Evaluating Equipment)

A method for evaluating equipment of the present disclosure is a method for evaluating nucleic acid detection equipment configured to detect nucleic acids, using a cell contained base produced by the method for producing a cell contained base of the present disclosure.

Using a cell contained base with a known number of nucleic acids having a specific base sequence located in at least one cell contained region, the method for evaluating equipment of the present disclosure can accurately evaluate the quantitativity and the detection accuracy of the equipment used. Moreover, it is possible to manage the equipment used, based on the method for evaluating equipment of the present disclosure.

EXAMPLES

The present disclosure will be described below more specifically by way of Examples. The present disclosure should not be construed as being limited to these Examples.

(gene Recombinant Yeast)

For producing a recombinant, a budding yeast w303-1a (product name: ATCC4001408, available from ATCC) was used as a carrier cell for 1 copy of a specific base sequence. The specific base sequence was a sequence specific to norovirus (NCBI, obtained from No. 0514004 issued by monitoring manager of food safety department (FIG. 20A and FIG. 20B), see Sequence No. 1). A gene recombinant yeast was produced by producing the specific base sequence in a tandem arrangement with URA3, which was a selectable marker, and introducing 1 copy of the specific base sequence into a yeast chromosome by homologous recombination, targeting a BAR1 region of the carrier cell.

(Culturing and Cell-Cycle Control)

Figure 21:
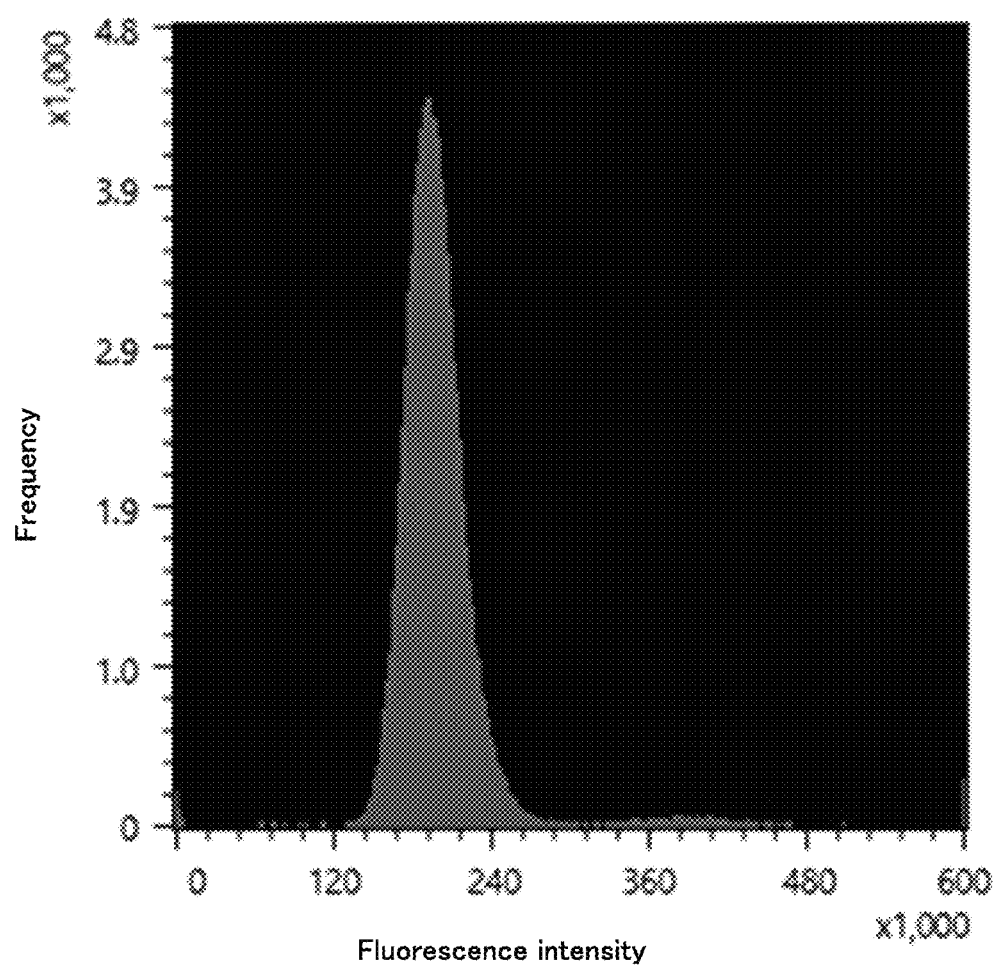
FIG. 21 is a graph plotting a flow cytometry result indicating yeast synchronization at a G0/G1 phase.

In an Erlenmeyer flask, a 90 mL fraction of the gene recombinant yeast cultured in 50 g/L of a YPD medium (product name: YPD MEDIUM, available from Clontech Laboratories, Inc.) was mixed with 900 microliters of a factor (available from Sigma-Aldrich Co., LLC, $\alpha$1-MATING FACTOR ACETATE SALT) prepared to 500 micrograms/mL with a Dulbecco's phosphate buffered saline (available from Thermo Fisher Scientific Inc., hereinafter may also be referred to as "DPBS") and incubated with a bioshaker (device name: BR-23F11, available from Taitec Corporation) at a shaking speed of 250 rpm at a temperature of 28 degrees C. for 2 hours, to synchronize the yeast at a G0/G1 phase, to obtain a yeast suspension. For confirmation of the cell cycle of the synchronized cells, the cells were stained with SYTOX GREEN NUCLEIC ACID STAIN (device name: 57020, available from Thermo Fisher Scientific Inc.) and subjected to flow cytometry using a flow cytometer (device name: SH1800, available from Sony Corporation) at an excitation wavelength of 488 nm. As a result, it was confirmed that the cells were synchronized at a G0/G1 phase. The ratio of cells at a G1 phase was 97.1% and the ratio of cells at a G2 phase was 2.9%. The results are plotted in FIG. 21.

(Immobilization)

Forty-five milliliters of the synchronization-confirmed yeast suspension was transferred to a centrifuge tube (VIOLAMO, product name: VIO-50R, available from As One Corporation) and centrifuged with a centrifugal separator (device name: CF16RN, available from Hitachi, Ltd.) at a rotation speed of 3,000 rpm for 5 minutes, with subsequent supernatant removal, to obtain yeast pellets. Four milliliters of formalin (available from Wako Pure Chemical Industries, Ltd., 062-01661) was added to the obtained yeast pellets, and the resultant was left to stand still for 5 minutes, then centrifuged with subsequent supernatant removal, and suspended with addition of 10 mL of ethanol, to obtain an immobilized yeast suspension.

(Staining)

Five hundred microliters of the immobilized yeast suspension was transferred to a 1.5 mL light-shielding tube (available from Watson, 131-915BR), centrifuged with a centrifugal separator at a rotation speed of 3,000 rpm for 5 minutes with subsequent supernatant removal, suspended sufficiently by pipetting with addition of 400 microliters of DPBS (1 mM EDTA) prepared to 1 mM EDTA (available from Tocris Bioscience, 200-449-4), then centrifuged with a centrifugal separator at a rotation speed of 3,000 rpm for 5 minutes with subsequent supernatant removal, to obtain yeast pellets. One milliliter of an Evans blue aqueous solution (available from Wako Pure Chemical Industries, Ltd., 054-04061) prepared to 1 mg/mL was added to the obtained pellets, and the resultant was stirred with a vortex for 5 minutes, then centrifuged with a centrifugal separator at a rotation speed of 3,000 rpm for 5 minutes with subsequent supernatant removal, and stirred with a vortex with addition of DPBS (1 mM EDTA), to obtain a stained yeast suspension.

(Dispersing)

The stained yeast suspension was subjected to dispersion treatment using an ultrasonic homogenizer (device name: LUH150, available from Yamato Scientific Co., Ltd.) at a power output of 30% for 10 seconds, centrifuged with a centrifugal separator at a rotation speed of 3,000 rpm for 5 minutes with subsequent supernatant removal, and then washed with addition of 1,000 microliters of DPBS. Centrifugal separation and supernatant removal were performed twice in total, and the resultant was finally suspended in DPBS, to obtain a yeast suspension ink.

(Dispensing and Cell Number Counting)

A cell contained base with known cell numbers was produced by counting the number of yeast cells in liquid droplets in the manner described below. Specifically, with the use of the liquid droplet forming device illustrated in FIG. 12, the yeast suspension ink was sequentially discharged into each cell contained region (well) of a 96 plate (product name: MICROAMP 96-WELL REACTION PLATE, available from Thermo Fisher Scientific Inc.), using a piezoelectricity applying-type discharging head (available in-house) as a liquid droplet discharging unit at 10 Hz. An image of yeast cells in a liquid droplet discharged was captured using a high-sensitivity camera (available from Tokyo Instruments Inc., SCMOS PCO.EDGE) as a light receiving unit and using a YAG laser (available from Spectra-Physics, Inc., EXPLORER ONE-532-200-KE) as a light source, and the cell number was counted by image processing with image processing software IMAGE J serving as a particle number counting unit for the captured image. In this way, a cell contained base with known cell numbers was produced.

(Extraction of Nucleic Acids)

With a Tris-EDTA (TE) buffer and ColE1 DNA (available from Wako Pure Chemical Industries, Ltd., 312-00434), ColE1/TE was prepared at 5 ng/microliter. With ColE1/TE, a Zymolyase solution of Zymolyase® 100T (available from Nacalai Tesque Inc., 07665-55) was prepared at 1 mg/mL. Four microliters of the Zymolyase solution was added into each cell contained region (well) of the produced cell contained base with known cell numbers, incubated at 37 degrees C. for 30 minutes, to dissolve cell walls (extraction of nucleic acids), and then thermally treated at 95 degrees C. for 2 minutes, to produce the cell contained base.

Aspects of the present disclosure are as follows, for example:

<1> A method for producing a cell contained base, the method including;
 a liquid droplet discharging step of discharging a cell suspension in the form of a liquid droplet with a liquid droplet discharging unit onto a base including at least one cell contained region;
 a cell number counting step of counting a number of cells contained in the liquid droplet with a plurality of sensors from two or more directions while the liquid droplet is flying into the cell contained region; and
 a liquid droplet landing step of landing the liquid droplet in the at least one cell contained region in a manner that a predetermined number of cells are located in the at least one cell contained region.

<2> The method for producing a cell contained base according to <1>,
 wherein the predetermined number is 10 or less.

<3> The method for producing a cell contained base according to <1> or <2>,
 wherein cell cycles of cells contained in the cell suspension are measured,
 wherein based on the measured cell cycles, a number of nucleic acids having a specific base sequence is estimated from a number of cells contained in the cell suspension, and wherein based on the estimated number of nucleic acids having a specific base sequence, a number of nucleic acids having a specific base sequence located in each of the at least one cell contained region is calculated.

<4> The method for producing a cell contained base according to <3>,
wherein a degree of certainty of the estimated number of nucleic acids is calculated.

<5> The method for producing a cell contained base according to any one of <1> to <4>,
wherein the sensors count the number of cells in the flying liquid droplet at a timing at which the liquid droplet is at a position that is immediately above the cell contained region.

<6> The method for producing a cell contained base according to any one of <1> to <5>,
wherein the sensors are installed in a region ranging from a discharging surface of the liquid droplet discharging unit, the region being present in a direction opposite to a direction in which the liquid droplet is discharged.

<7> The method for producing a cell contained base according to any one of <1> to <6>, further including
an outputting step of outputting the number of cells contained in the cell suspension that has landed in the cell contained region, by using values counted by the sensors.

<8> The method for producing a cell contained base according to any one of <1> to <7>,
wherein in the liquid droplet landing step, the liquid droplet is landed in the cell contained region in a manner that a plurality of levels are obtained.

<9> The method for producing a cell contained base according to any one of <1> to <8>,
wherein the cells are cells that can emit light in response to reception of light,
wherein the sensors are optical sensors configured to receive fluorescence from the cells in the liquid droplet, and
wherein the number of cells is calculated based on values counted by the optical sensors.

<10> The method for producing a cell contained base according to any one of <1> to <9>,
wherein the cells are a yeast.

<11> The method for producing a cell contained base according to any one of <1> to <10>,
wherein a volume average particle diameter of the cells is 100 micrometers or less in a free state.

<12> The method for producing a cell contained base according to any one of <1> to <11>,
wherein the cell suspension further contains a surfactant.

<13> The method for producing a cell contained base according to <12>,
wherein the surfactant is a nonionic surfactant.

<14> The method for producing a cell contained base according to <12> or <13>,
wherein a content of the surfactant is 0.001% by mass or greater but 30% by mass or less relative to a total amount of the cell suspension.

<15> The method for producing a cell contained base according to any one of <1> to <14>,
wherein discharging in the liquid droplet discharging step is performed by an on-demand method.

<16> The method for producing a cell contained base according to <15>,
wherein the on-demand method is a pressure applying method.

<17> The method for producing a cell contained base according to <16>,
wherein the pressure applying method is a method for applying a pressure to a liquid using a piezo element.

<18> The method for producing a cell contained base according to any one of <1> to <17>,
wherein the cell number counting step further includes an operation for observing cells before discharging.

<19> The method for producing a cell contained base according to any one of <1> to <18>,
wherein the cell number counting step further includes an operation for counting cells after landing.

<20> The method for producing a cell contained base according to any one of <1> to <19>, further including
a cell suspension producing step of producing the cell suspension containing a plurality of cells including the nucleic acid having a specific base sequence, and a solvent.

<21> The method for producing a cell contained base according to any one of <3> to <20>, further including
a nucleic acid number calculating step of calculating the number of nucleic acids contained in the cell contained region, based on at least any one of the cell cycles of cells, accuracy of the counted number of cells contained in the liquid droplet, and a ratio (accuracy) at which the liquid droplet lands within an intended range in the cell contained region.

<22> The method for producing a cell contained base according to any one of <1> to <21>, further including
a recording step.

<23> The method for producing a cell contained base according to any one of <1> to <22>, further including
a nucleic acid extracting step of extracting nucleic acids from the cells in the cell contained region,
wherein the method further includes an enzyme deactivating step after the nucleic acid extracting step.

<24> A method for evaluating equipment, the method including evaluating nucleic acid detection equipment configured to detect nucleic acids, using a cell contained base produced by the method for producing a cell contained base according to any one of <1> to <23>.

The method for producing a cell contained base according to any one of <1> to <23> and the method for evaluating equipment according to <24> can solve the various problems in the related art and can achieve the object of the present disclosure.

What is claimed is:

1. A method, comprising:
    discharging a cell suspension in a form of a liquid droplet with a liquid droplet discharging unit onto a base that comprises at least one cell contained region;
    counting a number of cells contained in the liquid droplet with a plurality of sensors from two or more directions while the liquid droplet is flying into the cell contained region;
    wherein said counting by said plurality of sensors occurs at a point at which the liquid droplet is at a position that is immediately above the cell contained region, and
    landing the liquid droplet in the at least one cell contained region in a manner that a predetermined number of cells are located in the at least one cell contained region.

2. The method according to claim 1,
    wherein said plurality of sensors is positioned lower than a position of a nozzle of the liquid droplet discharge unit.

3. The method according to claim 1, further comprising
    outputting the number of cells contained in the cell suspension that has landed in the cell contained region, by using values counted by the sensors.

4. The method according to claim 1,
    wherein said cell contained region comprises a plurality of levels and in the landing, the liquid droplet is landed in the cell contained region in a manner that a plurality of levels are obtained.

5. The method according to claim 1,
    wherein the cells comprise cells that emit light in response to reception of light,
    wherein said plurality of sensors comprise optical sensors configured to receive fluorescence from the cells in the liquid droplet, and
    calculating the number of cells based on values counted by the optical sensors.

6. The method according to claim 1,
    wherein the liquid droplet discharging unit is configured to discharge the liquid droplet on-demand.

7. The method according to claim 1, further comprising
    producing the cell suspension that comprises a plurality of cells that comprise a nucleic acid having a specific base sequence, and a solvent,
    wherein said producing occurs before said discharging.

8. The method according to claim 1, further comprising
    calculating an average value for the number of nucleic acids contained in the cell contained region, based on at least any one of the cell cycles of cells, accuracy of the counted number of cells contained in the liquid droplet, and a ratio at which the liquid droplet lands within an intended range in the cell contained region.

9. The method according to claim 1, further comprising before the discharging:
    determining the total number of cells and cell cycles of the cells contained in a cell suspension;
    estimating a number of nucleic acids having a specific base sequence based on the number of cells and cell cycles contained in the cell suspension; and after the landing,
    calculating a number of nucleic acids having a specific base sequence located in each of the at least one cell contained region based on the estimated number of the nucleic acids having a specific base sequence.

10. The method according to claim 1, further comprising after the landing:
    extracting the nucleic acids from the cells in the cell contained region.

11. A method, comprising:
    determining the total number of cells and cell cycles of the cells contained in a cell suspension, wherein the cell cycles of the cells contained in the cell suspension are measured by quantifying nuclear phases of the cells due to cell divisions;
    estimating a number of nucleic acids having a specific base sequence based on the number of cells and cell cycles contained in the cell suspension;
    discharging the cell suspension in a form of a liquid droplet with a liquid droplet discharging unit onto a base that comprises at least one cell contained region;
    counting a number of cells contained in the liquid droplet with a plurality of sensors from two or more directions while the liquid droplet is flying into the cell contained region;
    wherein said counting by said plurality of sensors occurs at a point at which the liquid droplet is at a position that is immediately above the cell contained region,
    landing the liquid droplet in the at least one cell contained region in a manner that a predetermined number of cells are located in the at least one cell contained region;

calculating a number of the nucleic acids having the specific base sequence located in each of the at least one cell contained region based on the estimated number of the nucleic acids having the specific base sequence; and extracting the nucleic acids from the cells in the cell contained region.

\* \* \* \* \*